United States Patent
Spears et al.

(10) Patent No.: US 11,649,477 B2
(45) Date of Patent: May 16, 2023

(54) ASSAYS AND REAGENTS FOR ANTIMICROBIAL SUSCEPTIBILITY TESTING

(71) Applicant: SELUX DIAGNOSTICS, INC., Charlestown, MA (US)

(72) Inventors: Benjamin Spears, Charlestown, MA (US); Kelly Flentie, Charlestown, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 737 days.

(21) Appl. No.: 16/506,729

(22) Filed: Jul. 9, 2019

(65) Prior Publication Data

US 2020/0040375 A1 Feb. 6, 2020

Related U.S. Application Data

(60) Provisional application No. 62/696,732, filed on Jul. 11, 2018.

(51) Int. Cl.
*C12Q 1/18* (2006.01)
*G01N 21/64* (2006.01)
*G01N 33/483* (2006.01)

(52) U.S. Cl.
CPC ........... *C12Q 1/18* (2013.01); *G01N 21/6408* (2013.01); *G01N 21/6428* (2013.01); *G01N 33/4833* (2013.01); *G01N 2201/0446* (2013.01)

(58) Field of Classification Search
CPC .................................................. G01N 21/6408
See application file for complete search history.

(56) References Cited

U.S. PATENT DOCUMENTS

| | | | | |
|---|---|---|---|---|
| 5,346,996 A | * | 9/1994 | Lehn | C07D 471/22 530/391.5 |
| 5,501,959 A | | 3/1996 | Lancaster et al. | |
| 9,834,808 B2 | | 12/2017 | Stern et al. | |
| 2006/0160166 A1 | | 7/2006 | Jiang et al. | |
| 2007/0212748 A1 | | 9/2007 | Sullivan et al. | |
| 2008/0132500 A1 | | 6/2008 | Liu et al. | |
| 2015/0064703 A1 | | 3/2015 | Super et al. | |
| 2017/0211121 A1 | | 7/2017 | Stern et al. | |
| 2018/0088141 A1 | | 3/2018 | Vacic et al. | |

FOREIGN PATENT DOCUMENTS

| WO | 2017197227 A1 | 11/2017 |
|---|---|---|
| WO | 2018119439 A | 6/2018 |

OTHER PUBLICATIONS

Syal et al., ACS Sensors, 2017, 2:1231-1239.*
Vourli et al., J Antimicrob Chemother., 2017, 72:2528-2530.*
International Search Report and Written Opinion for International application No. PCT/US2019/041046, dated Oct. 15, 2019, 27 pages.
Suling, W. J., and O'Leary, W. M., "Effect of Surfactants on Antibiotic Resistance", Antimicrobial Agents and Chemotherapy, 8(3):334-343 (1975).
Flentie, K., et al., "Microplate-based surface area assay for rapid phenotypic antibiotic susceptibility testing", Scientific Reports, 9:1-9(2019).
Tashyrev, O., and Preskrasna, I., "Express Method for Redox Potential and pH Measuring in Microbial Cultures", Inter J BIOautomation, 18(3):217-230 (2014).
Soon, R. L., et al., "Different Surface charge of colistin-susceptible and -resistant Acinetobacter baumannii cells measured with zeta potential as a function of growth phase and colistin treatment", J Antimicrob Chemother, 66:126-133 (2010).

* cited by examiner

*Primary Examiner* — Bin Shen
(74) *Attorney, Agent, or Firm* — Goodwin Procter LLP

(57) ABSTRACT

Systems and methods for antimicrobial susceptibility testing (AST) are provided in which variances in anionic charge of microbes are taken into account. Cationic surfactants may be used to sensitize otherwise resistant microorganisms to polycationic antibiotics, such as polymyxins. Since microorganisms gain polycationic antibiotic resistance through mutations that decrease surface anionic charge, the susceptibility of a microorganism to a polycationic antibiotic may be indicative of its surface charge. In order to enable electrostatic interactions with the microorganism surface, a cationic surfactant may be applied to increase the anionic charge of the microorganism.

22 Claims, 8 Drawing Sheets

US 11,649,477 B2

ASSAYS AND REAGENTS FOR ANTIMICROBIAL SUSCEPTIBILITY TESTING

CROSS REFERENCE TO RELATED APPLICATIONS

This application claims priority to U.S. Provisional Application No. 62/696,732, filed on Jul. 11, 2018, and titled "ASSAYS AND REAGENTS FOR ANTIMICROBIAL SUSCEPTIBILITY TESTING." The foregoing application is incorporated by reference herein in its entirety and for all purposes.

FIELD

The present disclosure relates to methods for antimicrobial susceptibility testing.

BACKGROUND

Antimicrobial-resistant microbial infections are associated with poor clinical outcomes including increased morbidity, mortality, and healthcare costs among infected patients. The prevalence of these organisms in such facilities in the United States has steadily increased over the last 30 years. Phenotypic antimicrobial susceptibility testing (AST) of microorganisms is critical for informing physicians of appropriate therapeutic regimens. Using current methods, AST determination typically requires a minimum of eight hours, rendering it an overnight process due to shift work in many clinical microbiology laboratories. While awaiting a determination from current AST methods, patients are often administered broad-spectrum antimicrobials which often have significant detrimental effects on patient health and/or contribute to the growing antimicrobial resistance epidemic. Furthermore, this time delay obtaining accurate antimicrobial treatment information increases patient stays in hospitals, thereby increasing costs and inconvenience to the patient.

Against this backdrop, government and industry stakeholder have proposed rules to promote antimicrobial stewardship in hospitals. However, antimicrobial stewardship efforts may be complicated by the limitations of current AST methods and antimicrobial prescribing practices. The inventors have previously disclosed a method for rapid AST, that may reduce the time required for AST determinations and facilitate antimicrobial stewardship. For example, AST systems and methods utilizing fluorescent probes that bind microorganism surfaces are described in commonly owned U.S. Pat. No. 9,834,808. These systems and methods are advantageous in that they address this need in a cost-effective manner and can be compatible with existing assay hardware components.

SUMMARY

The present disclosure provides improved rapid AST systems and methods that are robust to variations in microbial surface charge, for example due to the acquisition of antimicrobial resistance. In one aspect, this disclosure relates to a method for performing multi-assay rapid antimicrobial susceptibility testing (AST) sequences. This method may comprise inoculating a sample comprising a microorganism derived from a clinical sample into a plurality of wells of a test panel, at least one of the plurality wells comprising a cationic antimicrobial at a concentration above an epidemiological cutoff value, and at least one of the plurality of wells comprising no antimicrobial; incubating the test panel for a period of time; determining a ratio of growth of the microorganism in the at least one well of the test panel comprising the cationic antimicrobial relative to growth of the microorganism and if the ratio is above a predetermined threshold, contacting at least one of the remaining plurality of wells of the test panel with a surfactant; and performing at least one surface-area-based measurement of the sample in at least one of the remaining plurality of wells of the test panel.

In various embodiments, the surfactant may be selected from the group consisting of cetyl-trimethylammonium bromide (CTAB), octenidine dihydrochloride, cetylpyridinium chloride, benzalkonium chloride, dim ethyl dioctadecylammonium chloride, Methyltrialkyl($C_8$-$C_{10}$)ammonium chloride (adogen 464), benzethonium chloride, cetrimonium bromide, and dioctadecyldimethylammonium bromide. The method may further comprise the step of removing the surfactant from the at least one of the remaining plurality of wells prior to performing the at least one surface-area-based measurement. Performing the at least one surface-area-based measurement may comprise contacting the at least one remaining well with a cationic signaling agent. The cationic signaling agent may be a lanthanide cryptate, and performing the at least one surface-area-based measurement comprises detecting an association between the lanthanide cryptate and a surface of the microbe in the sample. The method may further comprise the step of contacting at least one of the remaining plurality of wells of the test panel with a surfactant selected from the group consisting of fatty alcohol ethoxylates, nonoxynols, octyl phenol ethoxylate (triton x-100), ethoxylated amines, poloxamers, glycerol monostearate, glycerol monolaurate, spans, tweens, alkyl polyglycosides, amine oxides, sulfoxides, and phosphine oxides if the ratio is below a predetermined threshold. The predetermined ratio may be 0.1, 0.2, 0.3, 0.4, 0.5 or 0.6. The predetermined ratio may be 0.2-0.4. The method may further comprise the step of assessing a level of growth in at least one of the plurality of wells of the test panel after the test panel is incubated for a period of time, and optionally incubating the test panel for an additional period of time if the level of growth does not reach a predetermined growth threshold.

In another aspect, this disclosure relates to a method for performing multi-assay rapid antimicrobial susceptibility testing (AST) sequences. This method may comprise inoculating a sample comprising a microorganism into a plurality of wells of a test panel, at least one of the plurality of wells comprising a polycationic antimicrobial at a concentration above an epidemiological cutoff value, and at least one of the plurality of wells comprising no antimicrobial; incubating the test panel for a period of time; determining a ratio of growth of the microorganism in the at least one well of the test panel comprising the cationic antimicrobial relative to growth of the microorganism in the at least one well comprising no antimicrobial; if the ratio is above a predetermined threshold, increasing an anionic charge density of a cell membrane of the microorganism; and measuring an association of a cationic signaling agent with the cell wall of the microorganism in at least one of the remaining plurality of wells of the test panel.

In various embodiments, the step of increasing the anionic charge density of the cell membrane of the microorganism may comprise contacting at least one of the remaining plurality of wells with a surfactant. The surfactant may be selected from the group consisting of cetyl-trimethylammonium bromide (CTAB), octenidine dihydrochloride, cetylpyridinium chloride, benzalkonium chloride, dimethyldioctadecylammonium chloride, Methyltrialkyl ($C_8$-$C_{10}$) ammonium chloride (adogen 464), benzethonium chloride, cetrimonium bromide, and dioctadecyldimethylammonium bromide. The method may further comprise the step of contacting at least one of the remaining plurality of wells of the test panel with a surfactant selected from the group consisting of fatty alcohol ethoxylates, nonoxynols, octyl phenol ethoxylate (triton x-100), ethoxylated amines, poloxamers, glycerol monostearate, glycerol monolaurate, spans, tweens, alkyl polyglycosides, amine oxides, sulfoxides, and phosphine oxides if the ratio is below the predetermined threshold.

In another aspect, this disclosure relates to a test panel for antimicrobial susceptibility testing. The test panel may comprise between 96 and 384 reservoirs, each reservoir configured to accommodate a fluid volume of 75-200 µl, at least one of the reservoirs comprising (a) at least 0.05, 0.1, 0.2, 0.3, 0.4, 0.5, 0.6, 0.7, 0.8, 0.9, 1.0, 1.1, 1.2, 1.3, 1.4, 1.5, 2, 2.5 or 3 µg of a polycationic antimicrobial, or (b) at least 5, 10, 15, 20, 25, 30, 35, or 40 µg of a polycationic antimicrobial. The polycationic antimicrobial may be colistin. The plurality of reservoirs may comprise an antimicrobial selected from a group of antimicrobials, and the plurality of reservoirs may define a dilution series for each of the group of antimicrobials. At least one reservoir may not include an antimicrobial agent.

In another aspect, this disclosure relates to a method for performing multi-assay rapid antimicrobial susceptibility testing sequences. This method may comprise inoculating a sample comprising a microorganism derived from a clinical sample into a plurality of wells of a test panel, the test panel comprising at least one growth control well lacking an antimicrobial agent, at least one anionic test well comprising a polycationic antimicrobial agent in an amount sufficient to result in a concentration, following inoculation, in excess of an epidemiological cutoff value, and a plurality of wells defining a plurality of dilution series for a plurality of antimicrobials; loading the test panel into an automated rapid antimicrobial susceptibility testing system for performing a multi-assay testing sequence; and operating the testing system to: incubate and agitate the inoculated sample in the incubation assembly; after a predetermined interval, or in response to a parameter of the sample in the growth control well, stopping incubation; determining a ratio of microbial growth in the anionic test well to growth control well and, if the ratio exceeds a predetermined threshold, contacting at least one of the remaining wells of the test panel with a surfactant at a concentration sufficient to disrupt a membrane of the microorganism without substantial lysis of the microorganism; and perform one or more endpoint cell surface assays on incubated samples in the test panel; measure an optical output from the samples in the plurality of wells of the test panel, the optical output corresponding to an amount of the microorganism remaining in each of the plurality of wells; and report at least one of: a minimum inhibitory concentration of and/or a qualitative susceptibility interpretation for the microorganism remaining in each of the plurality of wells and the plurality of antimicrobials.

In another aspect, this disclosure relates to a method for performing multi-assay rapid antimicrobial susceptibility testing sequences. This method may comprise inoculating a sample or subsample of a microbe containing patient material into a plurality of wells of a test panel, at least one test well comprising a cation-adjusted Mueller Hinton broth (MHB), at least one test well comprising Colistin, and a plurality of wells defining an antimicrobial dilution series; adding a metabolic indicator to the wells containing cation-adjusted MHB and Colistin and incubating the test panel under conditions suitable for microbe growth; reading the metabolic indicator as the fluorescent signal Ex560/Em590 to determine the background adjusted fluorescent signal; calculating an anionic ratio from the background subtracted fluorescent signal of samples grown in Colistin divided by the background subtracted fluorescent signal of samples grown in MHB; pretreating the wells defining the antimicrobial dilution series of the test panel, wherein if the anionic ratio is greater than a predetermined threshold, the step of pretreating comprises treating with cetyltrimethylammonium bromide and if the anionic ratio is less than the predetermined threshold, the step of pretreating comprises treating with phosphate-buffered saline with 1% Tween (PBST); applying a surface binding reagent; reading a time-resolved fluorescent signal in each of the plurality of wells of the antimicrobial dilution series; and based on the time-resolved fluorescent signal, determining a minimum inhibitory concentration (MIC) for an antimicrobial present in the test panel.

In various embodiments, the predetermined threshold may be between 0.05-0.3. The predetermined threshold may be 0.05, 0.1, 0.15, 0.2, and 0.25.

In another aspect, this disclosure relates to a method for performing multi-assay rapid antimicrobial susceptibility testing (AST) sequences. This method may comprise inoculating a sample comprising a microorganism derived from a clinical sample into a plurality of wells of a test panel comprising an ionic character assay, which comprises one or more wells comprising a cationic antimicrobial at a concentration at or above an epidemiological cutoff value or resistant breakpoint and one or more wells comprising no antimicrobial, incubating the test panel for a period of time, and determining an ionic character ratio of microorganism growth in the at least one well of the test panel comprising the cationic antimicrobial relative to growth of the microorganism in a well comprising no antimicrobial. If the ionic character assay ratio is above a predetermined threshold, at least one of the remaining plurality of wells of the test panel may be contacted with a surfactant, and at least one surface-area-based measurement of the sample in at least one of the remaining plurality of wells of the test panel may be performed.

In another aspect, this disclosure relates to a method for performing multi-assay rapid antimicrobial susceptibility testing (AST) sequences. This method may comprise inoculating a sample comprising a microorganism derived from a clinical sample into a plurality of wells of a test panel comprising an ionic character assay, which comprises one or more wells comprising a cationic antimicrobial at a concentration at or above an epidemiological cutoff value or resistant breakpoint and one or more wells comprising no antimicrobial, incubating the test panel for a period of time, determining an ionic character ratio of microorganism growth in the at least one well of the test panel comprising the cationic antimicrobial relative to growth of the microorganism in a well comprising no antimicrobial, and if the ionic character assay ratio is above a predetermined threshold, increasing an anionic charge density of a cell membrane of the microorganism, and measuring an association of a cationic signaling agent with the cell wall of the microorganism in at least one of the remaining plurality of wells of the test panel.

In various embodiments, the step of increasing the anionic charge density of the cell membrane of the microorganism may comprise contacting at least one of the remaining plurality of wells with a surfactant. The cationic antimicrobial in the ionic character assay may be polycationic. The cationic antimicrobial may include, but is not limited to, one or more of polymyxin A-E. The cationic antimicrobial may be one or more of colistin (polymyxin E) or polymyxin B. The lowest cationic antimicrobial concentration of the ionic character assay may be at or above 2 µg/mL. The lowest cationic antimicrobial concentration of the ionic character assay may be at or below 36 µg/mL. The ionic character assay may comprise two wells with different cationic antimicrobial concentrations. The ionic character assay may comprise colistin at 8 µg/mL and 16 µg/mL. The microorganism growth in the ionic character assay may be determined by absorbance and/or a metabolic indicator. The metabolic indicator may comprise resazurin. The resazurin concentration may be between 10 µM and 100 mM. The metabolic indicator may further comprise the metabolic probe formulation further comprises 1-methoxy-5-methlyphenazinium methyl sulfate (1-methoxy PMS) at a concentration between 50 µM and 1 M; methylene blue at a concentration between 100 nM and 5 µM; and each of ferrocyanide and ferricyanide at concentrations between 0.0001% and 0.1% (w/v). An incubation of 30 minutes to 6 hours may be performed following the addition of the metabolic indicator to a plurality of the ionic character assay wells.

In various embodiments, the method further may comprise performing a sufficient growth assay, comprising one or more control wells that comprises media but no antimicrobials and no microorganisms, and one or more assay wells that comprises media and microorganisms but no microorganisms, in which a metabolic indicator may be added within 2 hours of the onset of panel incubation to a plurality of the sufficient growth assays wells and a ratio of the absorbance and/or fluorescence in the assay-to-control wells is compared to a predetermined threshold, such that if the threshold is achieved sufficient growth is determined to have been achieved and if the threshold is not achieved the sample is incubated for a period of 30 minutes to 4 hours before the absorbance and/or fluorescence measurements are again performed and this process is repeated until the sufficient growth threshold is achieved or 12 hours have elapsed. The sufficient growth assay threshold may be 1, 1.05, 1.11, 1.15, 1.2. The metabolic indicator may comprise resazurin. The resazurin concentration may be between 10 µM and 100 mM. The metabolic indicator may further comprise the metabolic probe formulation further comprises 1-methoxy-5-methlyphenazinium methyl sulfate (1-methoxy PMS) at a concentration between 50 µM and 1 M; methylene blue at a concentration between 100 nM and 5 µM; and each of ferrocyanide and ferricyanide at concentrations between 0.0001% and 0.1% (w/v). The formulation of the metabolic indicator utilized for the ionic character assay may be approximately the same as that used for the sufficient growth assay. The ionic character assay may be performed in parallel with and using approximately the same metabolic indicator as a viability assay performed on a plurality of wells comprising dilution series of different antimicrobials in the panel. The surfactant added if the ionic character assay ratio is equal to or greater than the predetermined threshold may be selected from the group consisting of cetyl-trimethylammonium bromide (CTAB), octenidine dihydrochloride, cetylpyridinium chloride, benzalkonium chloride, dimethyldioctadecylammonium chloride, Methyltrialkyl($C_8$-$C_{10}$)ammonium chloride (adogen 464), benzethonium chloride, cetrimonium bromide, and dioctadecyldimethylammonium bromide. The surfactant may be CTAB. The CTAB concentration may be between 0.001% and 1%, e.g., between 0.01% and 0.1%. The formulation comprising the surfactant may further comprise a metal ion chelator. The metal ion chelator may be ethylenediaminetetraacetic acid (EDTA). The EDTA concentration may be between 0.001 and 1 M, 0.01 and 0.5 M.

In various embodiments, the method may further comprise the step of contacting at least one of the remaining plurality of wells of the test panel with a surfactant selected from the group consisting of fatty alcohol ethoxylates, nonoxynols, octyl phenol ethoxylate (triton x-100), ethoxylated amines, poloxamers, glycerol monostearate, glycerol monolaurate, spans, tweens, alkyl polyglycosides, amine oxides, sulfoxides, and phosphine oxides if the ionic character assay ratio is below the predetermined threshold. The surfactant may be tween-20 (polysorbate 20). The tween concentration may be between 0.001 and 1%. The predetermined threshold ratio of the ionic character assay may be 0.01, 0.05, 0.1, 0.2, 0.3, 0.4, 0.5 or 0.6. The predetermined threshold ratio may be 0.1-0.3. The method may further comprise the step of removing the surfactant from the at least one of the remaining plurality of wells prior to performing the at least one surface-area-based measurement. Performing the at least one surface-area-based measurement may comprise contacting the at least one remaining well with a cationic signaling agent. The cationic signaling agent may be a lanthanide cryptate, and performing the at least one surface-area-based measurement may comprise detecting an association between the lanthanide cryptate and a surface of the microbe in the sample. The microorganism may be gram-negative.

In another aspect, this disclosure relates to a test panel for antimicrobial susceptibility testing. This panel may comprise between 96 and 384 reservoirs, each reservoir configured to accommodate a fluid volume of 75-250 at least one of the reservoirs comprising (a) at least 0.05, 0.1, 0.2, 0.3, 0.4, 0.5, 0.6, 0.7, 0.8, 0.9, 1.0, 1.1, 1.2, 1.3, 1.4, 1.5, 2, 2.5 or 3 µg of a polycationic antimicrobial, or (b) at least 5, 10, 15, 20, 25, 30, 35, or 40 µg of a polycationic antimicrobial. The polycationic antimicrobial is a polymyxin. The polycationic antimicrobial may be colistin and/or polymyxin B. A plurality of reservoirs may comprise an antimicrobial selected from a group of antimicrobials, and the plurality of reservoirs may define a dilution series for each of the group of antimicrobials. At least one test panel may not include an antimicrobial agent.

In another aspect, this disclosure relates to a method for performing multi-assay rapid antimicrobial susceptibility testing sequences. This method may comprise inoculating a sample comprising a microorganism derived from a clinical sample into a plurality of wells of a test panel, with the exception of one or more negative control wells comprising growth media but no microorganism, the test panel comprising at least two positive growth wells lacking an antimicrobial agent, at least one ionic character well comprising a polycationic antimicrobial agent in an amount sufficient to result in a concentration, following inoculation, in excess of an epidemiological cutoff value or a resistant breakpoint, and a plurality of wells defining a plurality of dilution series for a plurality of antimicrobials. The method further may comprise loading the test panel into an automated rapid antimicrobial susceptibility testing system for performing a multi-assay testing sequence and operating the testing system to: add a metabolic indicator to the negative control and positive growth wells, the metabolic indicator comprising Resazurin at a concentration between 10 µM and 100 mM, 1-methoxy-5-methlyphenazinium methyl sulfate (1-methoxy PMS) at a concentration between 50 µM and 1 M, methylene blue at a concentration between 100 nM and 5 µM, and each of ferrocyanide and ferricyanide at concentrations between 0.0001% and 0.1% (w/v); incubate and optionally agitate the inoculated sample in the incubation assembly; after a predetermined interval or after achieving or surpassing a ratio of 1.0, 1.05, 1.1, 1.15, 1.2 of a sufficient growth assay, determined as the absorbance and/or fluorescence of the positive growth control-to-negative control wells, add a metabolic indicator into a plurality of wells including the ionic character assay well and a positive growth control well not used for the sufficient growth assay and perform an incubation of 30 or more minutes, the metabolic indicator comprising an approximately equivalent formulation to that used for the sufficient growth assay; determine the absorbance and/or fluorescence of a plurality of wells and calculate an ionic character assay ratio, defined as the ratio of microbial growth in the ionic character assay well(s)-to-growth control well(s) and, if the ratio equals or exceeds a predetermined threshold, contact at least one of the remaining wells of the test panel with a surfactant at a concentration sufficient to disrupt a membrane of the microorganism without substantial lysis of the microorganism, and, if the anionic character assay ratio is less than the predetermined threshold, contact at least one of the remaining wells of the test panel with a different surfactant; and perform one or more endpoint cell surface assays on incubated samples in the test panel; measure an optical output from the samples in the plurality of wells of the test panel, the optical output corresponding to an amount of the microorganism remaining in each of the plurality of wells; and report at least one of: a minimum inhibitory concentration of and/or a qualitative susceptibility interpretation for the microorganism remaining in each of the plurality of wells and the plurality of antimicrobials.

In another aspect, this disclosure relates to method for performing multi-assay rapid antimicrobial susceptibility testing sequences. This method may comprise inoculating a sample or cultured sample of microbe-containing patient material into a plurality of wells of a test panel, with the exception of one or more negative control wells comprising cation-adjusted Mueller Hinton broth (MHB) but no microorganism, of the inoculated wells at least two wells defining an ionic character assay, in which at least one test well comprises a MHB and colistin and at least one test well comprises MHB and no antimicrobial, and a plurality of wells defining multiple antimicrobial dilution series for different antimicrobials; incubating and optionally agitating the inoculated sample in the incubation assembly; after a predetermined interval or after achieving or surpassing a ratio of 1.0, 1.05, 1.1, 1.15, 1.2 of a sufficient growth assay, determined as the absorbance and/or fluorescence of the positive growth control-to-negative control wells, adding a metabolic indicator into a plurality of wells including the ionic character assay well and a positive growth control well not used for the sufficient growth assay and performing an incubation of 30 or more minutes, the metabolic indicator comprising an approximately equivalent formulation to that used for the sufficient growth assay and comprising: Resazurin at a concentration between 10 µM and 100 mM; 1-methoxy-5-methlyphenazinium methyl sulfate (1-methoxy PMS) at a concentration between 50 µM and 1 M; methylene blue at a concentration between 100 nM and 5 µM; and each of ferrocyanide and ferricyanide at concentrations between 0.0001% and 0.1% (w/v). The method may further comprise reading an absorbance at 550-650 nm to determine the absorbance signal and/or the metabolic indicator as the fluorescent signal Ex560/Em590 to determine the background adjusted fluorescent signal in a plurality of wells to which the metabolic indicator was added following achievement of the sufficient growth assay threshold; calculating a ionic character assay ratio from the background subtracted fluorescent signal of samples grown in Colistin divided by the background subtracted fluorescent signal of samples grown in MHB or the absorbance signal of samples growth in colistin divided by the signal of samples grown in MHB; pretreating the wells defining the antimicrobial dilution series of the test panel prior to the onset of a surface binding assay, wherein if the ionic character assay ratio is greater than a predetermined threshold, the step of pretreating comprises treating with CTAB and if the ionic ratio is less than the predetermined threshold, the step of pretreating comprises treating with phosphate-buffered saline with tween-20; applying a surface binding reagent; reading a time-resolved fluorescent signal in each of the plurality of wells of the antimicrobial dilution series; and based on the time-resolved fluorescent signal, determining a minimum inhibitory concentration (MIC) for an antimicrobial present in the test panel.

In various embodiments, the predetermined threshold may be between 0.1-0.3. The predetermined threshold may be 0.05, 0.1, 0.15, 0.2, and 0.25.

DESCRIPTION

Overview

Figure 1:
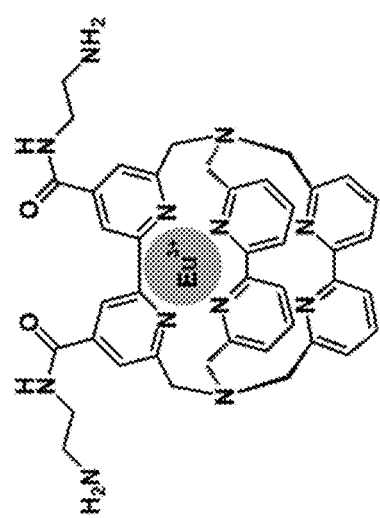
FIG. 1 depicts a europium-cryptate diamine probe.

The inventors have previously described systems and methods for rapid AST that utilize cationic, surface binding signaling agents such as the europium-cryptate diamine shown in FIG. 1. Without wishing to be bound by any theory, these signaling agents may, under suitable conditions, associate stoichiometrically with microbial cell membranes, allowing measurement of microbial growth with sufficient precision to differentiate between different growth modes, such as cell division versus filament formation or swelling.

Those of skill in the art will appreciate that certain microbes, such as *P. mirabilis* exhibit comparatively lower surface anionic charge relative to, e.g., *E. coli*. Additionally, certain mutations, such as those conferring resistance to cationic antimicrobials such as colistin, may reduce surface anionic charge. In each of these settings, changes in the anionic charge of the microbial cell membrane will result in changes in the level of binding of cationic signaling agents and, consequently, changes in the signal associated with such binding, which may complicate AST methods utilizing cationic signaling agents.

Again, without being bound by any theory, the inventors have found that certain cationic surfactants may increase the anionic charge of microbial cell membranes to facilitate binding of cationic signaling agents for rapid AST. However, not all cationic surfactants are compatible with rapid AST, and in some cases the use of a cationic surfactant may interfere with the binding of the cationic signaling agent. It should also be noted that cationic surfactants are used as exemplary throughout but nonionic and/or anionic surfactants may also be utilized.

Figure 6:
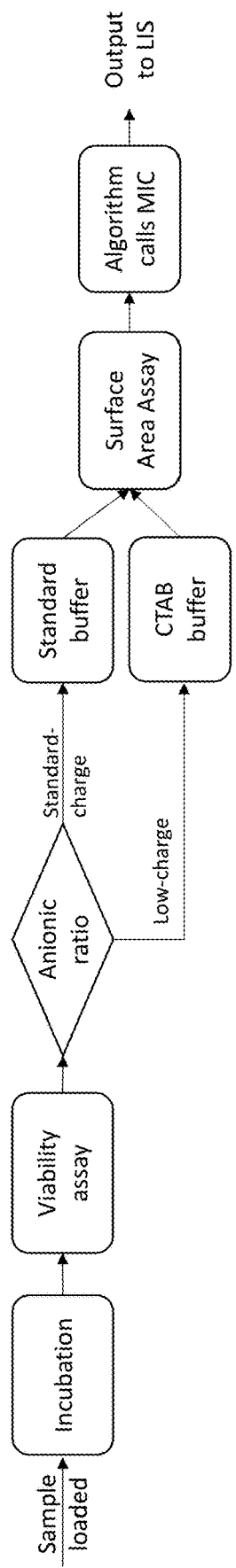
FIG. 6 depicts an exemplary AST method of the present disclosure which includes the steps of determining a relative anionic charge of a microorganism in a sample (e.g., an "anionic ratio") and, based on that determination, selecting a CTAB or other pretreatment prior to a surface area assay using a cationic probe such as europium cryptate diamine.

Rapid AST methods according to certain embodiments of the present disclosure involve the following steps, illustrated schematically in FIG. 6: first, inoculating a microbe-containing sample onto an AST test panel that includes a plurality of reservoirs, including (a) at least one reservoir that does not include an antimicrobial, or a growth control reservoir, and (b) at least one test reservoir that includes a reagent that differentially affects the growth of a microbe depending on its anionic surface charge—e.g., a reagent that reduces the growth of a microbe with a higher anionic charge relative to a microbe with a lower anionic surface charge.

The test panel also typically includes a plurality of reservoirs that define dilution series for a plurality of antimicrobials, and AST methods of this disclosure generally involve assessing microbial growth in each antimicrobial across the dilution series to determine a minimum inhibitory concentration and, optionally, a breakpoint concentration for each antimicrobial. Before microbial growth is assessed for the antimicrobial dilution series, the test panel is incubated for a period of time under conditions appropriate for microbial growth, e.g., at a temperature (in Celsius) of 25°, 30°, 35°, 37°, etc., optionally agitated during at least a portion of the incubation period. Following incubation, microbial growth is assessed in at least one growth control reservoir. If growth meets or exceeds a predetermined minimum level, an assessment of the anionic charge of the microbes is performed, for instance by comparing a level of growth in the test reservoir to that in the growth control reservoir. Based on this comparison, a sample preparation procedure is selected; for samples determined to have a low anionic charge, the sample preparation procedure includes the steps of treating the remaining reservoirs of the test panel with a cationic surfactant to associate the surfactant with microbial cell membranes in the reservoirs, and removing excess cationic surfactant prior to treating the reservoirs with a cationic detection reagent.

Reagents that differentially affect the growth of a microbe depending on its anionic surface charge can include, for example, cationic antimicrobials such as colistin. Certain forms of colistin resistance result in a decrease in the anionic charge of the cell membrane, reducing the efficacy of colistin and allowing microbes to survive exposures to concentrations above the clinical breakpoint concentration of colistin defined for colistin-susceptible microbes of the same strain. In some embodiments of this disclosure, where a microbe in a patient sample is known, the test well includes a quantity of colistin above the breakpoint concentration for the known microbe. In embodiments where the microbe is unknown, the test well includes a quantity of colistin above, e.g., a highest known or highest acceptable breakpoint concentration, and/or lowest known or lowest acceptable breakpoint concentration. Alternatively, the test panel includes a plurality of test wells defining a dilution series of colistin extending across the range of known or acceptable breakpoint concentrations. Other reagents that may differentially affect microbial growth based on anionic surface charge include polymyxin B, polymyxin E, cationic antimicrobial peptides, defensins and/or cathelicidins.

In some instances, rather than assessing anionic charge based on differential microbial growth in response to a reagent, the anionic charge is inferred from another known characteristic of the microbe. Certain gram-negative microorganisms, for example, may be more prone to colistin resistance than gram positive microorganisms, so a microorganism that is known be negative for gram staining may, in some embodiments of this disclosure, be assumed to be a low-anionic charge microorganism for purposes of the CTAB pretreatment determination. In other embodiments, the anionic charge of a microbe is inferred from assays of or for ATP, NAD, NADH, genetic material and/or enzymatic activity.

The cationic surfactant used in the methods of this disclosure may be cetyl-trimethylammonium bromide (CTAB), octenidine dihydrochloride, cetylpyridinium chloride, benzalkonium chloride, dimethyldioctadecylammonium chloride, Methyltrialkyl($C_8$-$C_{10}$)ammonium chloride (adogen 464), benzethonium chloride, cetrimonium bromide, or dioctadecyldimethylammonium bromide. In some instances, exposure to high concentrations of these surfactants may result in cell lysis, and free surfactant may associate with the cationic signaling reagent. Thus, in some embodiments of this disclosure, the cationic surfactant is applied to the AST test panel for a limited period of time, and/or at a concentration below that at which significant cell lysis is observed. Methods of this disclosure may include one or more rinses after the cationic surfactant is removed and before the cationic signaling agent is applied to the reservoirs of the test panel.

Microorganisms

An infection can include any infectious agent of a microbial origin, e.g., a bacterium, a fungal cell, an archaeon, and a protozoan. In some examples, the infectious agent is a bacterium, e.g., a gram-positive bacterium, a gram-negative bacterium, and an atypical bacterium. An antimicrobial resistant microorganism can be a microorganism that is resistant to an antimicrobial, i.e., anti-bacterial drugs, anti-fungal drugs, anti-archaea medications, and anti-protozoan drugs.

The microorganisms (e.g., a liquid suspension of microorganisms) may include one strain of microorganism. The microorganisms may include one species of microorganism. The microorganisms may include more than one strain of microorganism. The microorganisms may include one order of microorganism. The microorganisms may include one class of microorganism. The microorganisms may include one family of microorganism. The microorganisms may include one kingdom of microorganism.

The microorganisms (e.g., a liquid suspension of microorganisms) may include more than one strain of microorganism. The microorganisms may include more than one species of microorganism. The microorganisms may include more than one genus of microorganism. The microorganisms may include more than one order of microorganism. The microorganisms may include more than one class of microorganism. The microorganisms may include more than one family of microorganism. The microorganisms may include more than one kingdom of microorganism.

The microorganism may be a bacterium. Examples of bacterium include, but are not limited to, *Acetobacter aurantius, Acinetobacter bitumen, Acinetobacter* spp., *Actinomyces israelii, Actinomyces* spp., *Aerococcus* spp., *Agrobacterium radiobacter, Agrobacterium tumefaciens, Anaplasma, Anaplasma phagocytophilum, Azorhizobium caulinodans, Azotobacter vinelandii, Bacillus, Bacillus anthracis, Bacillus brevis, Bacillus cereus, Bacillus fusiformis, Bacillus licheniformis, Bacillus megaterium, Bacillus mycoides, Bacillus* spp., *Bacillus stearothermophilus, Bacillus subtilis, Bacillus Thuringiensis, Bacteroides, Bacteroides fragilis, Bacteroides gingivalis, Bacteroides melaninogenicus* (also known as *Prevotella melaninogenica*), *Bartonella, Bartonella henselae, Bartonella quintana, Bartonella* spp., *Bordetella, Bordetella bronchiseptica, Bordetella pertussis, Bordetella* spp., *Borrelia burgdorferi, Brucella, Brucella abortus, Brucella melitensis, Brucella* spp., *Brucella suis, Burkholderia, Burkholderia cepacia, Burkholderia mallei, Burkholderia pseudomallei, Calymmatobacterium granulomatis, Campylobacter, Campylobacter coli, Campylobacter fetus, Campylobacter jejuni, Campylobacter pylori, Campylobacter* spp., *Chlamydia, Chlamydia* spp., *Chlamydia trachomatis, Chlamydophila, Chlamydophila pneumoniae* (previously called *Chlamydia pneumoniae*), *Chlamydophila psittaci* (previously called *Chlamydia psittaci*), *Chlamydophila* spp., *Clostridium, Clostridium botulinum, Clostridium difficile, Clostridium perfringens* (previously called *Clostridium welchii*), *Clostridium* spp., *Clostridium tetani, Corynebacterium, Corynebacterium diphtheriae, Corynebacterium fusiforme, Corynebacterium* spp., *Coxiella burnetii, Ehrlichia chaffeensis, Ehrlichia* spp., *Enterobacter cloacae, Enterobacter* spp., *Enterococcus, Enterococcus avium, Enterococcus durans, Enterococcus faecalis, Enterococcus faecium, Enterococcus gallinarum, Enterococcus maloratus, Enterococcus* spp., *Escherichia coli, Francisella* spp., *Francisella tularensis, Fusobacterium nucleatum, Gardenerella* spp., *Gardnerella vaginalis, Haemophilius* spp., *Haemophilus, Haemophilus ducreyi, Haemophilus influenzae, Haemophilus parainfluenzae, Haemophilus pertussis, Haemophilus vaginalis, Helicobacter pylori, Helicobacter* spp., *Klebsiella pneumoniae, Klebsiella* spp., *Lactobacillus, Lactobacillus acidophilus, Lactobacillus bulgaricus, Lactobacillus casei, Lactobacillus* spp., *Lactococcus lactis, Legionella pneumophila, Legionella* spp., *Leptospira* spp., *Listeria monocytogenes, Listeria* spp., *Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium* spp., *Mycobacterium tuberculosis, Mycoplasma, Mycoplasma fermentans, Mycoplasma genitalium, Mycoplasma hominis, Mycoplasma penetrans, Mycoplasma pneumoniae, Mycoplasma* spp., *Neisseria, Neisseria gonorrhoeae, Neisseria meningitidis, Neisseria* spp., *Nocardia* spp., *Pasteurella, Pasteurella multocida, Pasteurella* spp., *Pasteurella tularensis, Peptostreptococcus, Porphyromonas gingivalis, Prevotella melaninogenica* (previously called *Bacteroides melaninogenicus*), *Proteus* spp., *Pseudomonas aeruginosa, Pseudomonas* spp., *Rhizobium radiobacter, Rickettsia, Rickettsia prowazekii, Rickettsia psittaci, Rickettsia quintana, Rickettsia rickettsii, Rickettsia* spp., *Rickettsia trachomae, Rochalimaea, Rochalimaea henselae, Rochalimaea quintana, Rothia dentocariosa, Salmonella, Salmonella enteritidis, Salmonella* spp., *Salmonella typhi, Salmonella typhimurium, Serratia marcescens, Shigella dysenteriae, Shigella* spp., *Spirillum volutans, Staphylococcus, Staphylococcus aureus, Staphylococcus epidermidis, Staphylococcus* spp., *Stenotrophomonas maltophilia, Stenotrophomonas* spp., *Streptococcus, Streptococcus agalactiae, Streptococcus avium, Streptococcus bovis, Streptococcus cricetus, Streptococcus faecium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus* spp., *Treponema, Treponema denticola,*

*Treponema pallidum, Treponema* spp., *Ureaplasma* spp., *Vibrio, Vibrio cholerae, Vibrio comma, Vibrio parahaemolyticus, Vibrio* spp., *Vibrio vulnificus, viridans* streptococci, *Wolbachia, Yersinia, Yersinia enterocolitica, Yersinia pestis, Yersinia pseudotuberculosis*, and *Yersinia* spp.

The microorganism may be a fungus. Examples of fungi include, but are not limited to, *Aspergillus* spp., *Blastomyces* spp., *Candida* spp., *Cladosporium, Coccidioides* spp., *Cryptococcus* spp., *Exserohilum, fusarium, Histoplasma* spp., *Issatchenkia* spp., mucormycetes, *Pneumocystis* spp., ringworm, scedosporium, *Sporothrix*, and *Stachybotrys* spp. The microorganism may be a protozoan. Examples of protozoans include, but are not limited to, *Entamoeba histolytica, Plasmodium* spp., *Giardia lamblia*, and *Trypanosoma brucei*.

Antimicrobials

When the microorganism is a bacterium, exemplary antimicrobials include Amikacin, Aminoglycoside, Aminoglycoside amoxicillin, Aminoglycosides, Amoxicillin, Amoxicillin/clavulanate, Ampicillin, Ampicillin/sulbactam, Antitoxin, Arsphenamine, Azithromycin, Azlocillin, Aztreonam, β-lactam, Bacitracin, Capreomycin, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftaroline, Ceftaroline fosamil, Ceftazidime, Ceftibuten, Ceftizoxime, Ceftobiprole, Ceftriaxone, Cefuroxime, Cephalosporin, Chloramphenicol, Chloramphenicol(Bs), Ciprofloxacin, Clarithromycin, Clindamycin, Clofazimine, Cloxacillin, Colistin, Co-trimoxazole, Cycloserine, Dalbavancin, Dapsone, Daptomycin, Demeclocycline, Dicloxacillin, Dirithromycin, Doripenem, Doxycycline, Enoxacin, Ertapenem, Erythromycin, Ethambutol, Ethambutol(Bs), Ethionamide, Flucloxacillin, Fluoroquinolone, Fluoroquinolones, Fosfomycin, Furazolidone, Fusidic acid, Gatifloxacin, Geldanamycin, Gemifloxacin, Gentamicin, Grepafloxacin, Herbimycin, Imipenem/Cilastatin, Isoniazid, Kanamycin, Levofloxacin, Lincomycin, Linezolid, Lomefloxacin, Loracarbef, Macrolides, Mafenide, Meropenem, Methicillin, Metronidazole, Mezlocillin, Minocycline, Moxifloxacin, Mupirocin, Nafcillin, Nafcillin, Nalidixic acid, Neomycin, Netilmicin, Nitrofurantoin(Bs), Norfloxacin, Ofloxacin, Oritavancin, Oxacillin, Oxytetracycline, Paromomycin, Penicillin, Penicillin G, Penicillin V, Piperacillin, Piperacillin/tazobactam, Platensimycin, Polymyxin B, Posizolid, Pyrazinamide, Quinupristin/Dalfopristin, Radezolid, Raxibacumab, Rifabutin, Rifampicin, Rifampin, Rifapentine, Rifaximin, Roxithromycin, Silver sulfadiazine, Sparfloxacin, Spectinomycin, Spectinomycin (Bs), Spiramycin, Streptogramins, Streptomycin, Sulbactam, Sulfacetamide, Sulfadiazine, Sulfadimethoxine, Sulfamethizole, Sulfamethoxazole, Sulfanilimide, Sulfasalazine, Sulfisoxazole, Sulfonamidochrysoidine, Tedizolid, Teicoplanin, Teixobactin, Telavancin, Telithromycin, Temafloxacin, Temocillin, Tetracycline, Thiamphenicol, ticarcillin, Ticarcillin/clavulanate, Ticarcillin/clavulanic acid, Tigecycline, Tigecycline(Bs), Tinidazole, TMP/SMX, Tobramycin, Torezolid, Trimethoprim(Bs), Trimethoprim-Sulfamethoxazole, Troleandomycin, Trovafloxacin, Vancomycin, and generics thereof or a variant thereof.

Antimicrobials whose interactions with the microorganism affect and are affected by the negative charges on the microorganism surface can include: polycationic aminoglycosides, which upon binding the cell surface displace $Mg^{2+}$ ions, which bridge lipid membrane components, thereby disrupting the outer membrane and enhancing drug uptake; cationic polymyxins (colistin and polymyxin B), whose binding to the microorganism cell is also dependent on the membrane's negative charge and for which both mutational and plasmid-mediated resistance occurs by reducing membrane negative charge; and daptomycin, a lipopeptide that resembles host innate immune response cationic antimicrobial peptides and requires $Ca^{2+}$ and phosphatidyl glycerol for its membrane-disrupting mechanism of action and for which resistance can also involve alteration in cell surface charge.

When the microorganism is a fungus, exemplary antimicrobials include 5-fluorocytosine, Abafungin, Albaconazole, Allylamines, Amphotericin B, Ancobon, Anidulafungin, Azole, Balsam of Peru, Benzoic acid, Bifonazole, Butoconazole, Candicidin, Caspofungin, Ciclopirox, Clotrimazole, Cresemba, Crystal violet, Diflucan, Echinocandins, Econazole, Efinaconazole, Epoxiconazole, Fenticonazole, Filipin, Fluconazole, Flucytosine, Grifulvin V, Griseofulvin, Gris-Peg, Haloprogin, Hamycin, Imidazoles, Isavuconazole, isavuconazonium, Isoconazole, Itraconazole, Ketoconazole, Lamisil, Luliconazole, Micafungin, Miconazole, Natamycin, Noxafil, Nystatin, Omoconazole, Onmel, Oravig, Oxiconazole, Posaconazole, Propiconazole, Ravuconazole, Rimocidin, Sertaconazole, Sporanox, Sulconazole, Terbinafine, Terconazole, Thiazoles, Thiocarbamate antifungal, Tioconazole, Tolnaftate, Triazoles, Undecylenic acid, Vfend, Voriconazole, and generics thereof or a variant thereof.

When the microorganism is a protozoan, exemplary antimicrobials include 8-Aminoquinoline, Acetarsol, Agents against amoebozoa, Ailanthone, Amodiaquine, Amphotericin B, Amprolium, Antitrichomonal agent, Aplasmomycin, Arsthinol, Artelinic acid, Artemether, Artemether/lumefantrine, Artemisinin, Artemotil, Arterolane, Artesunate, Artesunate/amodiaquine, Atovaquone, Atovaquone/proguanil, Azanidazole, Azithromycin, Benznidazole, Broxyquinoline, Buparvaquone, Carbarsone, Carnidazole, Chiniofon, Chloroquine, Chlorproguanil, Chlorproguanil/dapsone, Chlorproguanil/dapsone/artesunate, Chlorquinaldol, Chromalveolate antiparasitics, Cinchona, Cipargamin, Clazuril, Clefamide, Clioquinol, Coccidiostat, Codinaeopsin, Cotrifazid, Cryptolepine, Cycloguanil, Dehydroemetine, Difetarsone, Dihydroartemisinin, Diloxanide, Diminazen, Disulfiram, Doxycycline, Eflornithine, ELQ-300, Emetine, Etofamide, Excavata antiparasitics, Fumagillin, Furazolidone, Glycobiarsol, GNF6702, Halofantrine, Hydroxychloroquine, Imidocarb, Ipronidazole, Jesuit's bark, KAF156, Lumefantrine, Maduramicin, Mefloquine, Megazol, Meglumine antimoniate, Melarsoprol, Mepacrine, Metronidazole, Miltefosine, Neurolenin B, Nicarbazin, Nifurtimox, Nimorazole, Nitarsone, Nitidine, Nitrofural, Olivacine, Ornidazole, Oroidin, Pamaquine, Paromomycin, Pentamidine, Pentavalent antimonial, Phanquinone, Phenamidine, Piperaquine, Primaquine, Proguanil, Project 523, Propenidazole, Pyrimethamine, Pyronaridine, Quinfamide, Quinine, Ronidazole, Schedula Romana, SCYX-7158, Secnidazole, Semapimod, Sodium stibogluconate, Spiroindolone, Sulfadoxine, Sulfadoxine-Pyrimethamine, Sulfalene, Suramin, Tafenoquine, Teclozan, Tenonitrozole, Tilbroquinol, Tinidazole, Trimetrexate, Trypanocidal agent, Warburg's tincture, and generics thereof or a variant thereof.

An antimicrobial may be a drug that operates by a mechanism similar to a herein-recited drug. Other antimicrobial drugs known in the art may be used in the methods described herein.

Liquid Suspensions

The liquid may include a growth media, such as cation-adjusted Mueller Hinton broth. This media may comprise an additive, known to those skilled in the art to promote microorganism growth, and stability. In addition to different antimicrobials, different test wells may comprise an additive known to improve AST accuracy for specific antimicrobials. For example, additional sodium chloride may be added to tests comprising oxacillin and additional calcium may be added to tests comprising daptomycin.

Biological Samples

The microorganisms described herein may be derived from biological samples. In some embodiments, the biological sample is any sample that comprises a microorganism, e.g., a bacterium and a fungal cell. The biological sample may be derived from a clinical sample.

Exemplary biological samples can include, but are not limited to, whole blood, plasma, serum, sputum, urine, stool, white blood cells, red blood cells, buffy coat, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchoalveolar lavage, bronchial lavage, or pulmonary lavage, lung aspirates, and organs and tissues, including but not limited to, liver, spleen, kidney, lung, intestine, brain, heart, muscle, pancreas, and the like, swabs (including, without limitation, wound swabs, buccal swabs, throat swabs, nasal swabs, vaginal swabs, urethral swabs, cervical swabs, rectal swabs, lesion swabs, abscess swabs, nasopharyngeal swabs, and the like), and any combination thereof. Also included are bacteria cultures or bacteria isolates, fungal cultures or fungal isolates. The ordinary-skilled artisan may also appreciate that isolates, extracts, or materials obtained from any of the above exemplary biological samples are also within the scope of the present invention.

Microorganisms obtained from a biological sample may be cultured or otherwise processed as is routinely performed in the art.

Controls Used in AST Methods

Controls may include antimicrobials for which the microorganism is not susceptible. As examples, if the assay is used to determine the susceptibility of gram-positive bacteria, then the controls (and the test incubations) may include one or more antimicrobials that target gram-negative bacteria, and if the assay is used to determine the susceptibility of eukaryotic microorganisms, the control (and the test incubations) may include one or more antibacterial antimicrobials.

In some embodiments, the control is a positive control measured from microorganisms under otherwise identical conditions but without antimicrobials or with one or more antimicrobials for which the microorganisms are not susceptible. In some embodiments, the control is measured from microorganisms under otherwise identical conditions but without nutrients. In some embodiments, the control is measured from microorganisms under otherwise identical conditions with one or more toxins known to inhibit growth of the microorganisms.

Controls may be historic controls. In some embodiments, the test incubations are performed after control incubations have been performed. In some embodiments, controls are performed in a cartridge distinct from the cartridge comprising the test incubations.

Cartridges

A cartridge can be a container that is capable of holding and allowing growth of a liquid suspension of microorganisms. Non-limiting examples of a cartridge can include a culture flask, a culture dish, a petri dish, a bioassay dish, a culture tube, a test tube, a microfuge tube, a bottle, a microchamber plate, a multi-chamber plate, a microtiter plate, a microplate. The cartridge may comprise one chamber. The cartridge may include a plurality of chambers, each chamber being a space capable of holding a liquid suspension in physical isolation from another space; an example of a chamber is a chamber in a multiwall plate. The cartridge may comprise 1, 2, 3, 4, 5, 6, 7, 8, 9, 10, 11, 12, 24, 48, 96, 192, 384, 1536, or more chambers, and any number of chambers in between. The bottom of the cartridge chamber may be flat, round, or V-shaped.

Antimicrobials present within a plurality of chambers on the cartridge can be suspended in a medium. In some embodiments, the antimicrobial is present in the form of antimicrobial film. In certain embodiments, the antimicrobial is in solid form. In some embodiments, the solid antimicrobial is lyophilized and/or dried. Certain embodiments provide for one or more antimicrobials present in one or more cartridge chambers as antimicrobial films, in solid form, lyophilized, or dried prior to introduction of a suspension of microorganisms.

An antimicrobial dilution series may be frozen, lyophilized, or prepared fresh prior to plate inoculation with a sample. In some cases, inoculation of cartridges can be performed either by hand or using an automated system. In some examples, such as in cases of fresh antimicrobial plates, an automated liquid handling system may be used to prepare the cartridge with antimicrobial dilution series. Inoculation processes can include any of various processes that may be known in the art.

As described herein, cartridges can be used to contain various combinations of fluids in order to carry out multiple testing sequences, such as a check point assay and a plurality of different growth assays. In some embodiments, a cartridge has a set of chambers used to facilitate the one or more checkpoint assays and a set of chambers used to facilitate the one or more growth assays. By way of example, a cartridge can include an array of chambers arranged in rows and columns. The cartridge can include a set of control chambers and a set of antimicrobial testing chambers. The set of control chambers can include two chambers and the set of testing chambers can include the remainder of chambers along the plate. In some embodiments, the set of control chambers includes at least two chambers, where one chamber is a growth chamber and another chamber is a no-growth chamber. In some embodiments, the growth chamber includes, or be inoculated to include, a combination of broth and a patient sample such that the microorganisms in the patient sample can grow within the broth during an incubation period. In certain embodiments, antimicrobials are not added to the checkpoint assay chamber. Whereas, in some embodiments, the no-growth chamber can include, or be inoculated to include, broth without the patient sample (i.e., broth in the absence of the microorganisms from the patient sample). In some embodiments, antimicrobials are also not added to the no-growth chamber. Thus, during an incubation period, the no-growth chamber can serve as a baseline as compared to the growth chamber in which the microorganisms can grow.

In some embodiments, each cartridge includes a "test panel," a plurality of antimicrobials distributed across multiple wells in a defined dilution series for each antimicrobial (e.g., a 2-fold dilution series, a 10-fold dilution series, etc.). In addition, each cartridge or test panel can contain control chambers, such as a growth control chamber, a no growth (contamination) control chamber and/or a saline control chamber. The saline control chamber can represent FIT control approximately equal to the initial concentration of microorganism in inoculum. The cartridges can include multiple chambers (e.g., 96 chamber cartridge or 384 chamber cartridge) with a cover (e.g., a removable lid) and an identifier (e.g., a bar code) that uniquely defines antibiotic configuration and a unique code, which defines the plate and can be associated with a unique patient sample conforming to HIPAA.

The testing chambers can include any of various combinations of the patient sample and various types and concentrations of antimicrobials for which susceptibility can be analyzed. Rows of chambers can be dedicated to a particular antimicrobial and concentrations of that antimicrobial can vary between columns of the same row. For example, a cartridge can have a row of chambers containing penicillin where each chamber from left to right contains an increasing concentration of penicillin.

Of course, other examples are possible. For example, the different chambers and sets of chambers can be positioned at any of various locations along a cartridge. Additionally, the different sets of chambers (e.g., control chambers and testing chambers) can include greater or fewer individual chambers along the cartridge. Additionally, in some cases, not all chambers are used/occupied during testing.

Automated AST Methods

The methods described herein can be performed in an automated manner using commercially available equipment, custom made equipment, or a combination thereof. Automating the methods allows for performance of a greater number of assays as well as increased consistency among assays. Automation can also increase speed and resolution of these methods.

Surface-Binding Probe Assays

Surface-binding assays (also referred to as surface-binding probe assays) can utilize a signaling agent. Signaling agents typically comprise a moiety capable of binding to a microorganism (e.g., an antibody and/or a lectin that bind to a microorganism surface, a charged moiety and/or a functional moiety that non-specifically binds to the microorganism surface) and a chemical moiety capable of providing a signal or contributing to production of a signal (e.g., an enzyme chemiluminophore, and lanthanide chelate). Exemplary enzymes include horseradish peroxidase, alkaline phosphatase, acetyl cholinesterase, glucose oxidase, beta-D-galactosidase, beta-lactamase, and a combination thereof.

A signal generator may include one or more chemical moieties conjugated to one or more microorganism receptors. Signal generators include, but are not limited to, one or more catalysts (including enzymes, metal-oxide nanoparticles, organometallic catalysts, nanoparticles designed for signal amplification (such as those described in the U.S. Provisional Applications to which the present application claims priority and incorporates by reference in their entireties), bacteriophages comprising signal generating elements, fluorophores (including organic fluorophores, europium, or ruthenium(II), rhenium(I), palladium(II), platinum(II)-containing organometallics), and/or colorimetric dyes (including organic stains). Combinations of the above may be used, such as nanoparticles, dendrimers, and/or other nanoscale structures with enzymes, fluorophores, and/or organometallic molecules.

The chemical moiety may be conjugated to a signaling agent before contacting the signaling agent to a microorganism, while the signaling agent is initially contacted to a microorganism, or after the signaling agent has contacted a microorganism.

When the signaling agents are added to AST dilutions containing a microorganism, signaling agent receptors (e.g., moieties that can bind specifically or non-specifically to a microorganism) may associate with microorganism surfaces. Thus, the more intact microorganisms, for example, there are in solution, the greater the number of signaling agents that will be associated with these bacteria. Consequently, there is an inverse relationship between the number of intact bacteria and the number of signaling agents that are free in solution, as defined by those not bound to intact bacteria. Note that free signaling agents may be bound to soluble microbial components if, for example, microorganisms lyse in response to antimicrobial treatment.

The number of signaling agents that associate with and/or intercalate into microorganism surfaces is proportional to the microorganism surface area. Microorganism surface area is strongly associated with truly resistant microorganisms. In particular, in the case of microorganisms that swell or elongate in response to MIC- and sub-MIC concentrations of antimicrobials (e.g., filament forming bacteria), metabolic and/or volumetric identifications are known to give false susceptibility profiles for rapid AST time points, defined as those less than six hours. To overcome this limitation, the present invention translates microorganism surface area (rather than volume) into a measurable signal such as an optical signal. The methods described herein are able to accurately determine microorganism resistance profiles in less than six hours.

In order to separate signaling agents associated with and/or intercalated into microorganisms from free signaling agents, it may be necessary to perform one or more separation and/or competitive binding steps. Such steps include, but are not limited to, centrifugation (e.g., with a g-force >500×g), filtration (e.g., via a filter having pores smaller than or equal to 0.45 microns, or smaller than or equal to 0.2 microns), electrophoresis, and/or magnetic capture; such steps are well-known to those skilled in the art.

In order to promote signaling agent binding and/or reduce background, it may further be advantageous, before adding signaling agents, to separate microorganisms from the liquid in which they were suspended during incubation. Such separations may include but are not limited to, centrifugation, filtration, electrophoresis, and/or magnetic capture.

Signaling agents may be added together with microorganisms and/or antimicrobials, such that they are present for the entire AST incubation period. This total period may be up to twenty-four hours, or within eight hours, or within five hours. Alternatively, signaling agents may be added to microorganisms and antimicrobial after a prescribed incubation period. This period may be up to twenty-four hours, or within eight hours, or within four hours.

Signaling agents are designed to associate with and/or intercalate in microorganism surfaces, including walls and/or membranes. Signaling agents designed for association comprise binding moieties including, but not limited to, one or more antibodies, lectins, other proteins, small molecules with one or more charged chemical groups, small molecules with one or more functional chemical groups, phages, glycoproteins, peptides, aptamers, charged small molecules, small molecules with fixed charges, charged polymers, charged polymers with fixed charges, hydrophobic small molecules, charged peptide, charged peptides with fixed charges, peptides with alternating hydrophilic and hydrophobic regions, and/or small molecule ligands, which may or may not be organometallic complexes. Molecules designed for microorganism association are well-known to those skilled in the art. Signaling agents may remain bound to microorganisms and/or may be internalized, thus all associations are included. Signaling agents designed for intercalation may include, but are not limited to, small hydrophobic molecules, hydrophobic peptides, and/or peptides with alternating hydrophobic and hydrophilic regions. Molecules designed for microorganism intercalation are well-known to those skilled in the art. Signaling agents may further be specific to one or more types of microorganisms. Signaling agents may have multiple receptors. These may enhance binding and/or enable simultaneous binding to two or more microorganisms, which may further serve to agglutinate bacteria. Prior to or concurrently with the addition of signaling agents it may be advantageous to adjust the solution pH. This may be beneficial for enhancing charge-charge interactions between microorganisms and signaling agents. The anionic charge of microorganisms may be increased by titrating the solution pH above neutral (more basic). It may thus be beneficial to utilize moieties with one or more fixed, cationic charges.

It is noteworthy that the signaling agent may specifically bind to a microorganism (e.g., an antibody that specifically binds to a microorganism species or a strain of microorganism) or my non-specifically binds to a microorganism (e.g., by a generic covalent or non-covalent bond formation and another non-specific chemical association known in the art).

Alternately, chemicals and/or biochemicals which are capable of associating with signaling agents may be added to the liquid in which the microorganisms are suspended during growth, such that chemicals and/or biochemicals are incorporated into microorganisms during incubation. This may serve to enhance signaling agent association with microorganisms. In alternative embodiments, the signaling agents themselves may be present in the liquid in which the microorganisms are suspended during incubation and may be incorporated into microorganisms during growth.

The signaling agents can comprise an amplifier signal generator (amplifier group), such that the signal from each intact microorganism may be amplified beyond the number of signaling agents associated with each microorganism. For example, the enzyme horseradish peroxidase (HRP) is known to be able to amplify signals $>1\times10^4$-fold. Thus, if one hundred HRP molecules are bound to each microorganism surface, an amplification of $10^6$ may be achieved. This may increase the speed with which AST determinations may be made by enabling discrimination of microorganism concentrations that cannot otherwise be differentiated. Use of Europium formulations similarly provides signal amplification.

Alternatively, the signaling agents may comprise optical dye precursors known to those skilled in the art as membrane dyes that are designed to greatly increase fluorescence emission upon intercalation into a hydrophobic region, such as a cell membrane. Assays designed with these signaling agents may require microorganisms to be concentrated into a smaller volume, approaching a plane, to produce sufficient signals so as to be easily optically measured. Interfering species may require the use of near-IR fluorophores.

Exemplary amplifier groups include those described in, e.g., International Publication No. WO 2016/015027 and in International Application No. PCT/US16/42589, each of which is incorporated by reference in its entirety. An amplifier group can comprise a catalyst, a fluorophore, a colormetric dye, an enzyme, a catalyst, or a nanoparticle. Exemplary fluorophores include those described in FIG. 1, Table 1 of International Application No. PCT/US16/42589, which is incorporated by reference in its entirety. An amplifier group can comprise a lanthanide. Lanthanides include, but are not limited to, is europium, strontium, terbium, samarium, or dysprosium.

An amplifier group can comprise an organic fluorophore, e.g., a coordination complex. The coordination complex can be europium coordination complex, a ruthenium coordination complex, a rhenium coordination complex, a palladium coordination complex, a platinum coordination complex. An amplifier can comprise a chemiluminophore, a quantum dot, an enzyme, an iron coordination catalyst, a europium coordination complex, a ruthenium coordination complex, a rhenium coordination complex, a palladium coordination complex, a platinum coordination complex, a samarium coordination complex, a terbium coordination complex, or a dysprosium coordination complex.

In some embodiments, an amplifier group comprises a moiety that is:

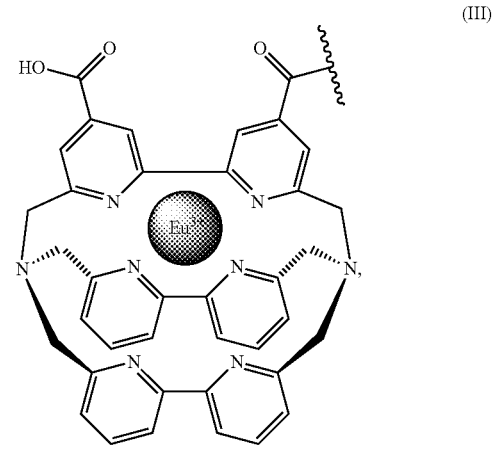

(III)

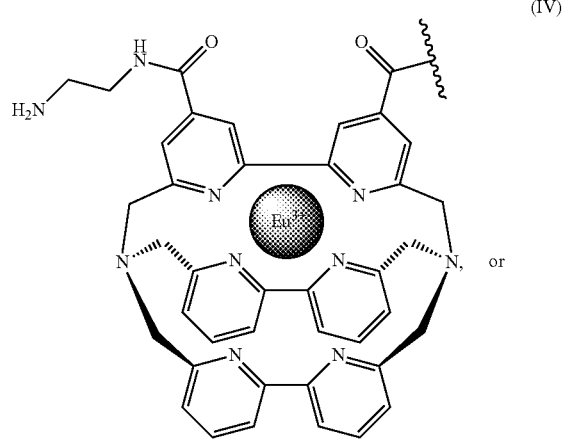

(IV)

or

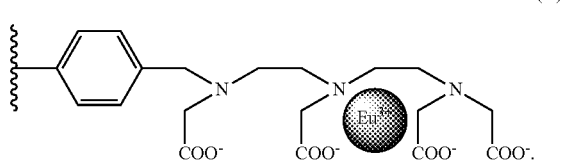

(V)

In some embodiments, an amplifier group comprises a moiety that is:

(VI)

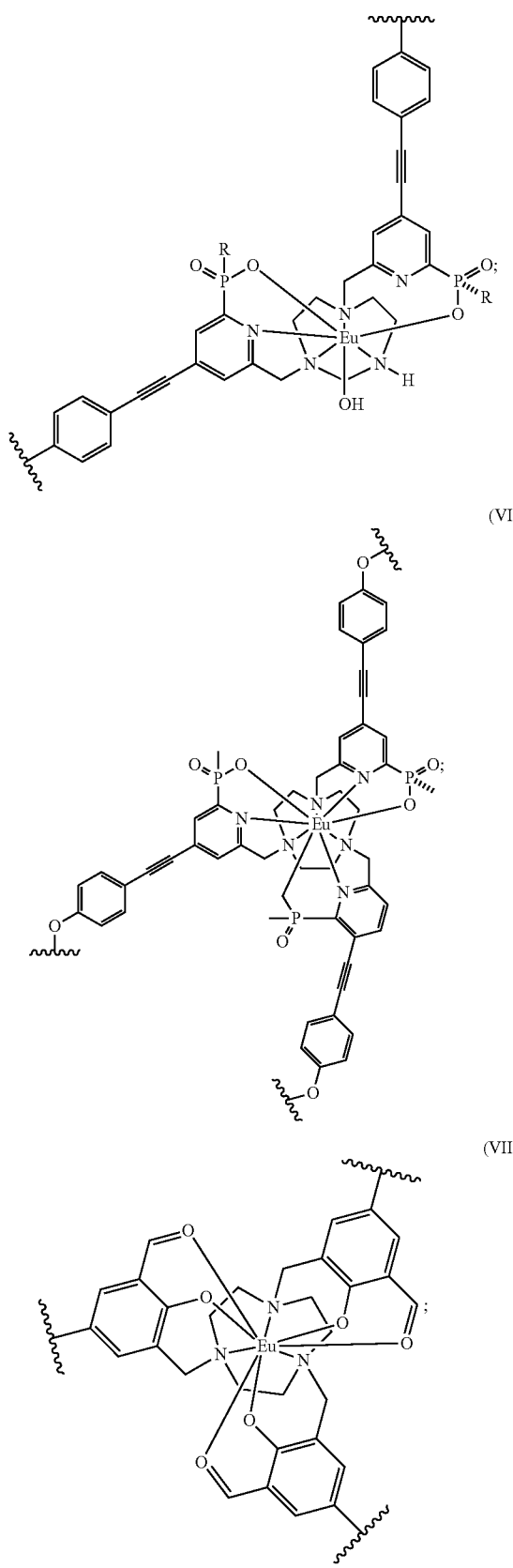

(IX)

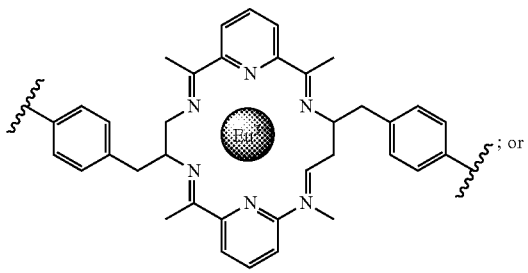

; or (X)

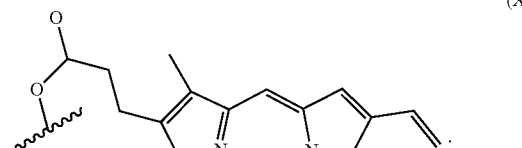

An amplifier group can comprise a fluorophore or colormetric dye. Suitable fluorophores and colormetric dyes are well known to those skilled in the art and are described in *The Molecular Probes® Handbook: A Guide to Fluorescent Probes and Labeling Technologies*, 11th Ed. (2010) and Gomes, Fernandes, and Lima *J. Biochem. Biophys. Methods* 65 (2005) pp 45-80, which are herein incorporated by reference in their entirety. Exemplary fluorophores also include those described in, e.g., International Publication No. WO 2016/015027 and in International Application No. PCT/US16/42589, each of which is incorporated by reference in its entirety.

Examples of suitable fluorophore or colormetric dyes include, but are not limited to, ethidium bromide, propidium iodide, SYTOX green, phenanthridines, acridines, indoles, imidazoles, cyanine, TOTO, TO-PRO, SYTO, 5-carboxy-2, 7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-ROX (carboxy-X-rhodamine), 6-Carboxyrhodamine 6G, 7-Amino-4-methylcoumarin, 7-Aminoactinomycin D (7-AAD), 7-Hydroxy-4-methylcoumarin, 9-Amino-6-chloro-2-methoxyacridine, ACMA (9-Amino-6-chloro-2-methoxyacridine), Acridines, Alexa Fluors, Alizarin, Allophycocyanin (APC), AMCA (Aminomethylcoumarin), Bodipy, Carboxy-X-rhodamine, Catecholamine, Fluorescein (FITC), Hydroxycoumarin, Lissamine Rhodamine, Monobromobimane, Oregon Green, Phycoerythrin, SYTO, Thiadicarbocyanine (DiSC3), Thioflavin, X-Rhodamine, C or TetramethylRodamineIsoThioCyanate.

An amplifier group can comprise an organometallic compound, transition metal complex, or coordination complex. Examples of such amplifier groups include, but are not limited to, those described in EP 0 180 492, EP 0 321 353, EP 0 539 435, EP 0 539 477, EP 0 569 496, EP139675, EP64484, U.S. Pat. Nos. 4,283,382, 4,565,790, 4,719,182, 4,735,907, 4,808,541, 4,927,923, 5,162,508, 5,220,012, 5,324,825, 5,346,996, 5,373,093, 5,432,101, 5,457,185, 5,512,493, 5,527,684, 5,534,622, 5,627,074, 5,696,240, 6,100,394, 6,340,744, 6,524,727, 6,717,354, 7,067,320, 7,364,597, 7,393,599, 7,456,023, 7,465,747, 7,625,930, 7,854,919, 7,910,088, 7,955,859, 7,968,904, 8,007,926, 8,012,609, 8,017,254, 8,018,145, 8,048,659, 8,067,100, 8,129,897, 8,174,001, 8,183,586, 8,193,174, 8,221,719, 8,288,763, 8,362,691, 8,383,249, 8,492,783, 8,632,753, 8,663,603, 8,722,881, 8,754,206, 8,890,402, 8,969,862, 9,012,034, 9,056,138, 9,118,028, 9,133,205, 9,187,690, 9,193,746, 9,312,496, 9,337,432, 9,343,685, 9,391,288, and 9,537,107, which are incorporated by reference in their entirety. Exemplary organometallic compounds, transition metal complexes, or coordination complexes also include those described in, e.g., International Publication No. WO 2016/015027 and in International Application No. PCT/US16/42589, each of which is incorporated by reference in its entirety.

In some embodiments, amplifier group is a lanthanide coordination complex such as a complex between a lanthanide (e.g., Eu or Tb) and a tetradentate ligand or a complex between a lanthanide (e.g., Eu or Tb) and a cryptate ligand.

In some embodiments, amplifier group is a coordination complex of Lanthanum (La), Cerium (Ce), Praseodymium (Pr), Neodymium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Ruthenium (Ru), Rhodium (Rh), Palladium (Pd), Osmium (Os), Iridium (Ir), or Platinum (Pt). In some embodiments, amplifier group is a coordination complex of a rare earth metal collectively refers to 17 elements consisting of a group of 15 elements from lanthanum having an atomic number of 57 to lutetium having an atomic number of 71 (lanthanides), and two additional elements consisting of scandium having an atomic number of 21 and yttrium having an atomic number of 39. Specific examples of rare earth metals include europium, terbium, lanthanum, cerium, praseodymium, neodymium, promethium, samarium, gadolinium, dysprosium, holmium, erbium, thulium, ytterbium, lutetium, scandium and yttrium. In some embodiments, amplifier group is a coordination complex of a lanthanide (e.g., Europium or Terbium) with diethylenetriaminetetraacetic acid or cryptate ligand.

Specific examples of a signaling agent include, but are not limited to, moieties comprising:

(1)

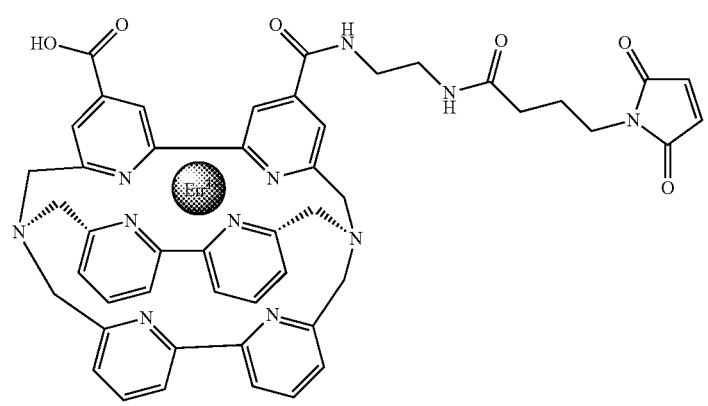

Eu-cryptate-maleimide (2)

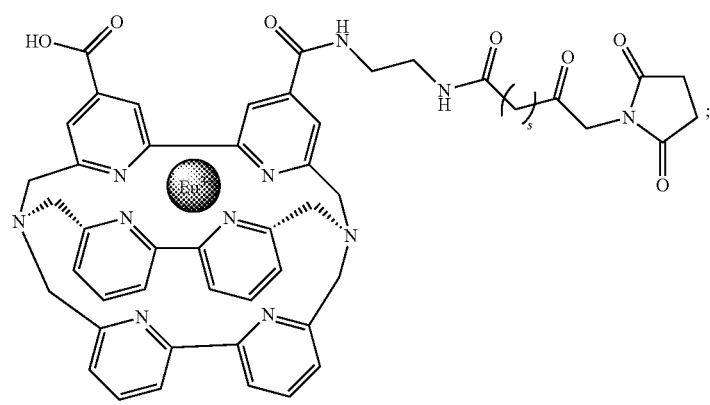

Eu-cryptate-NHS

-continued
(3)
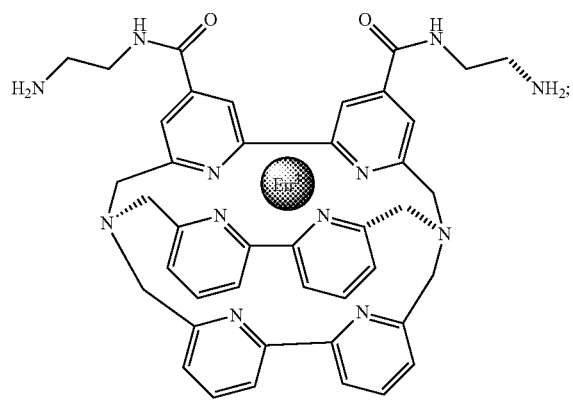
Eu-cryptate-diamine
(4)
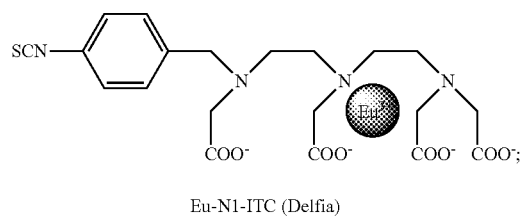
Eu-N1-ITC (Delfia)
(5)
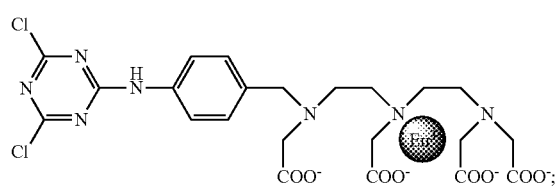
Eu-N1-DTA
(6)
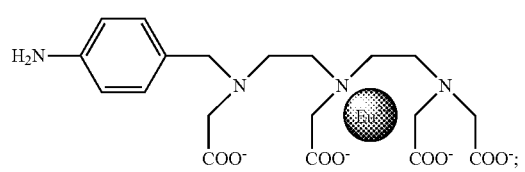
Eu-N1-amino
(7)
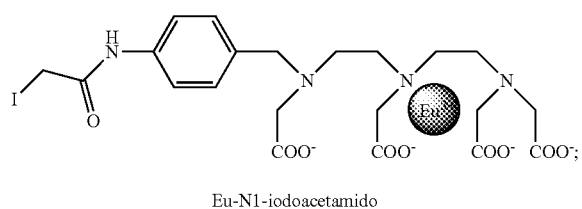
Eu-N1-iodoacetamido
(8)
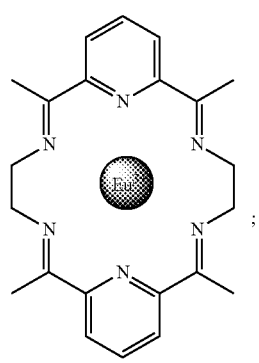
(9)
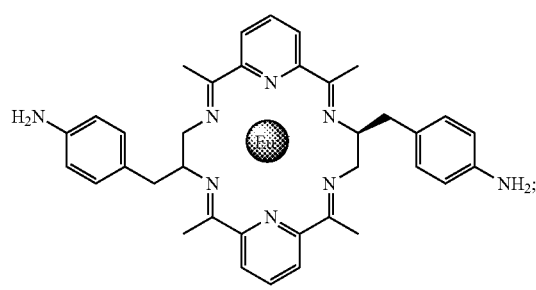
(10)
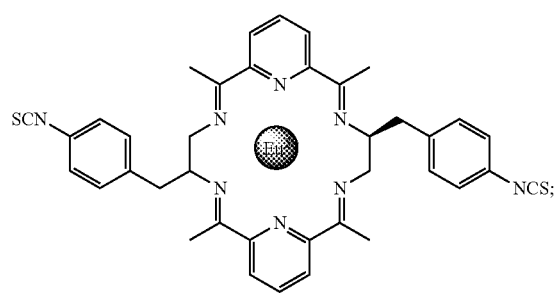
(11)
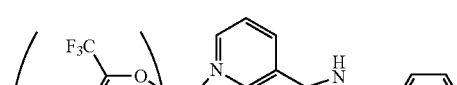

A signaling agent can comprise a luminophore (donor) which features high luminescence quantum efficiency and long luminescence decay time (>100 ns). Exemplary luminophores are cationic, metalorganic complexes of palladium, rhodium, platinum, ruthenium, osmium, rare earths (in particular, europium and lanthanum). The organic portion of these metalorganic complexes may consist, for example, of ligands from the group of porphyrins, bipyridyls, phenanthrolines or other heterocyclical compounds.

In some embodiments, a signaling agent capable of binding a microorganism surface comprises an antibody (e.g., monoclonal or polyclonal), modified antibodies (e.g., biotinylated monoclonal antibody, biotinylated polyclonal antibody, europium chelate-antibody, horseradish peroxidase-conjugated antibody), antibody variants (e.g., Fab: fragment, antigen-binding (one arm); F(ab')$_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), WGA-Biotin, PolymixinB-Biotin, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In some embodiments, a signaling agent capable of binding a microorganism surface comprises or is formed from a structure comprising an antibody, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In some embodiments, a signaling agent capable of binding a microorganism surface comprises an amplifier group that comprises a lanthanide coordination complex, and/or an enzyme and streptavidin and/or an antibody and/or aptamer. In some embodiments, a signaling agent capable of binding a microorganism surface comprises a binding moiety comprising a polyclonal and/or monoclonal antibody.

In some embodiments, a signaling agent capable of binding a microorganism surface comprises a binding moiety comprising a modified antibody. Exemplary modified antibodies include a biotinylated monoclonal antibody, biotinylated polyclonal antibody, a europium chelate-antibody, and a horseradish peroxidase-conjugated antibody. In some embodiments, a signaling agent capable of binding a microorganism surface comprises a binding moiety comprising an antibody variant. Exemplary antibody variants include Fab: fragment, antigen-binding (one arm); F(ab')$_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), In some embodiments, a signaling agent capable of binding a microorganism surface comprises WGA-Biotin or PolymixinB-Biotin. In some embodiments, a signaling agent capable of binding a microorganism surface comprises a binding moiety comprising a synthetic and/or natural ligand and/or peptide. In some embodiments, a ligand and/or peptide is selected from bis(zinc-dipicolylamine), TAT peptide, serine proteases, cathelicidins, cationic dextrins, cationic cyclodextrins, salicylic acid, lysine, and combinations thereof. In some embodiments, a signaling agent capable of binding a microorganism surface comprises a binding moiety comprising a synthetic and/or natural polymer and/or glycopolymer. In embodiments, a natural and/or synthetic polymer is linear or branched and selected from amylopectin, Poly(N-[3-(dimethylamino)propyl] methacrylamide), poly(ethyleneimine), poly-L-lysine, poly [2-(N,N-dimethylamino)ethyl methacrylate], and combinations thereof. In some embodiments, a natural and/or synthetic polymer and/or glycopolymer comprises moieties including, but not limited to, chitosan, gelatin, dextran, trehalose, cellulose, mannose, cationic dextrans and cyclodextrans, quaternary amines, pyridinium tribromides, histidine, lysine, cysteine, arginine, sulfoniums, phosphoniums, or combinations thereof including, but not limited to, co-block, graft, and alternating polymers. In some embodiments, a signaling agent capable of binding a microorganism surface comprises a binding moiety comprising a glycoprotein selected from mannose-binding lectin, other lectins, annexins, and combinations thereof.

In some embodiments, a signaling agent capable of binding to a microorganism surface comprises: an antibody; and a europium coordination complex. In some embodiments, a signaling agent capable of binding to a microorganism surface comprises a linker group L that comprises NH$_2$-PEG-Biotin (2K), NH$_2$-PEG-Biotin (4K), sulfo-NHS-Biotin, WGA-Biotin, or polymixinB-Biotin. In some embodiments, a signaling agent capable of binding to a microorganism surface comprises a europium complex comprises:

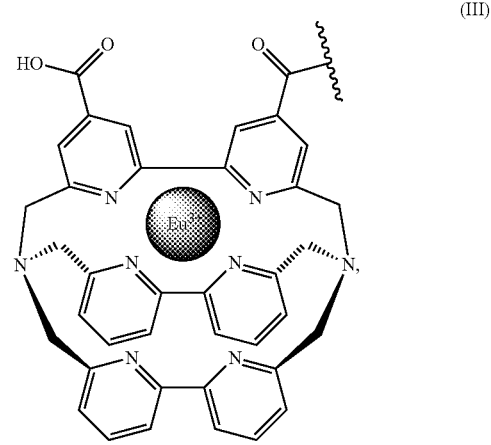

(III)

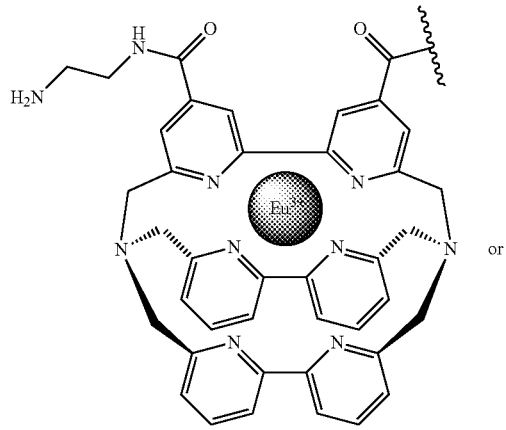

(IV)

or

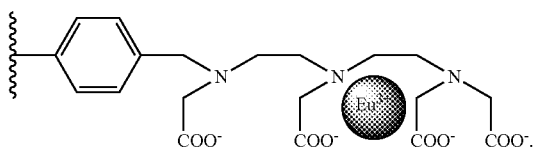

(V)

In some embodiments, a signaling agent capable of binding to a microorganism surface comprises a europium complex comprises:

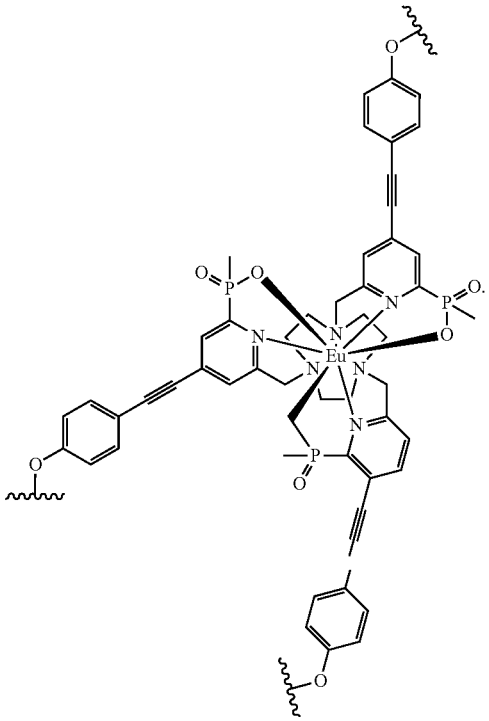

; or

Alternatively, the signaling agents may be part of a pair, such as FRET/TR-FRET donor and acceptors or singlet oxygen pairs consisting of a photosensitizer and detector. Assays designed with these signaling agents may require the separation of the microorganisms from the initial growth media, with subsequent resuspension into a desired reaction buffer prior to the addition of the signaling reagents. Conversely, assays designed with these signaling agents may require no separation steps due to the required relative distance necessary to generate a signal.

Examples of FRET/TR-FRET donors include, but are not limited to, Lanthanide (Eu, Sm, Dy, or Tb)-containing cryptate organometallic (CisBio), Lance Eu-W1024 (Perkin Elmer), Lance Eu-W8044 (Perkin Elmer), also any organic fluorescent pair donor.

Examples of FRET/TR-FRET acceptors include, but are not limited to, matched organic dyes, such as ULight dye (Perkin Elmer), SureLight APC (Perkin Elmer), allophycocyanin, Cy5, d2 dye (CisBio), also any organic fluorescent pair acceptor.

Examples of singlet oxygen photosensitizers include, but are not limited to, methuselah Green Carboxy (Ursa Bio), Sensitizer Blue (Ursa Bio), rose Bengal, Erythrosin B, methylene blue, chlorophylls, AlphaBead donor (Perkin Elmer).

Examples of singlet oxygen detectors include, but are not limited to, singlet oxygen detector green (ThermoFisher), trans-1-(2'-methoxyvinyl)pyrene, Si-DMA (Dojindo), AlphaBead acceptor (Perkin Elmer).

Examples of incorporators include, but are not limited to, ethynyl-D-alanine (EDA), azido-D-alanine (ADA), fluorescent D-alanines described in *Angew Chem Int Ed Engl.* 2012 Dec. 7; 51(50): 12519-12523.

EXAMPLES

Example 1: Low Anionic Charge Organisms are not Bound by the Europium-Cryptate-Diamine Probe Bacteria—*E. coli* and *P. mirabilis*—were grown in nutrient broth (MHB) or saline (negative control) and bound with the europium probe. Bacteria were prepared by diluting colonies into saline to reach a McFarland value of 0.5, which was verified using a spectrophotometer, diluted, and inoculated into 96-well plates containing cation-adjusted Mueller Hinton broth or saline. Plates were incubated at 35° C., shaking at 150 rpm for 3 hours, after which 10 µl of Alamar Blue were added to each well and plates were incubated for 1 additional hour. After this incubation, 100 µl of a Phosphate-Buffered Saline (PBS) with 1% Tween-20 was added to each well. The plates were placed on a shaker at 450 RPM for 10 minutes, followed by centrifugation at 2500×g for 2.5 minutes. The wells were aspirated and 100 µL PBS with 0.05% Tween-20 (PBST) was added back into the wells. Ten microliters of Eu-cryptate-diamine (5 ng/well) was added to each well and the plates were shaken for 10 minutes. The plates were then centrifuged, the wells aspirated, and 200 µL 1×PBST were added to each well. These steps were repeated twice. After the final wash, time-resolved fluorescence for all wells was read at 330/615 nm.

Figure 2:
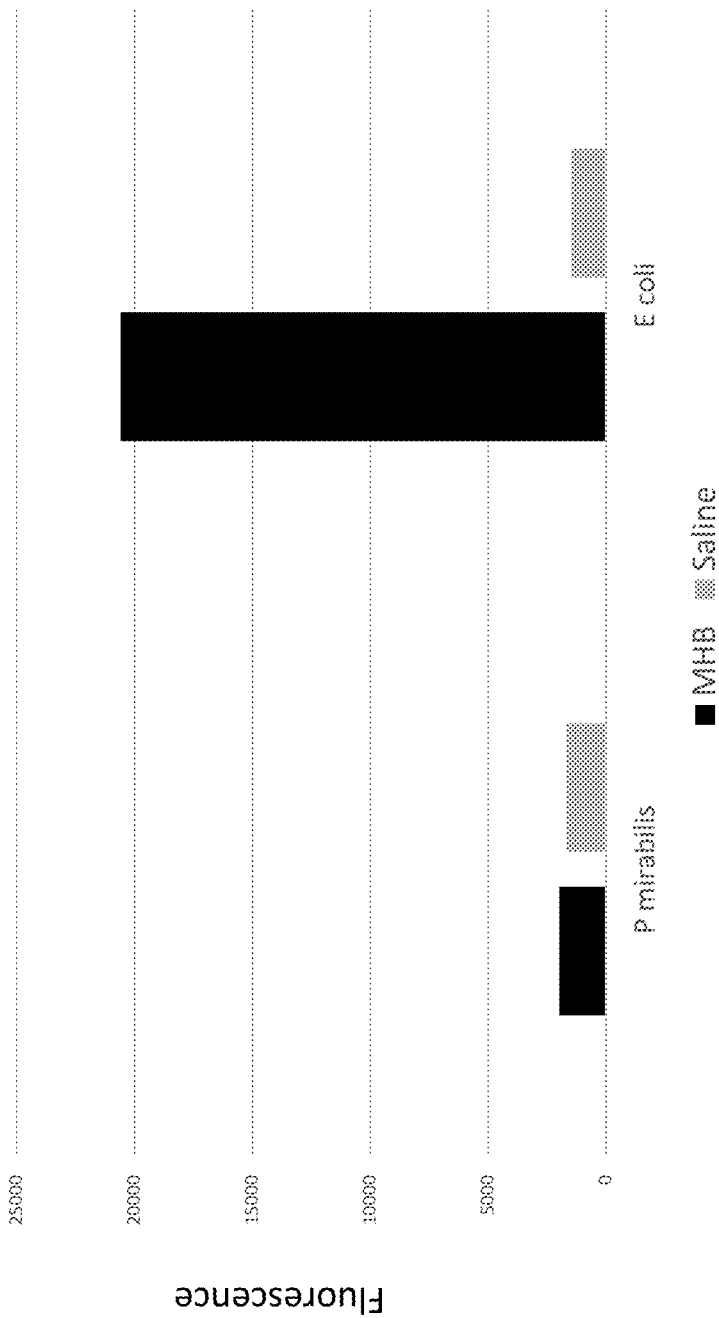
FIG. 2 shows time-resolved fluorescence (TRF) signals at 330/615 nm for a microorganism with a standard surface anionic charge, *E coli*, and a microorganism with low anionic charge, *P. mirabilis*, each incubated in either Mueller Hinton broth (MHB) or saline. *E. coli* is bound well by the europium probe, and therefore shows a high signal in conditions where bacteria grew (MHB) vs conditions where no growth occurred (saline). However, the low anionic charge organism *P. mirabilis* demonstrates a low TRF signal in both MHB and saline conditions, indicating poor binding of the Europium probe.

As shown in FIG. 2, *E. coli* is bound well by the europium probe, and therefore shows a high signal in conditions where bacteria grew (MHB) vs conditions where no growth occurred (saline). However, the low anionic charge organism *P. mirabilis* demonstrates a low TRF signal in both MHB and saline conditions, indicating poor binding of the Europium probe.

Example 2: The Cationic Surfactant CTAB Renders Low Anionic Charge Organisms Able to be Bound by Europium-Cryptate-Diamine

*P. mirabilis* bacteria were prepared by diluting colonies into saline to reach a McFarland value of 0.5, which was verified using a spectrophotometer, diluted, and inoculated into 96-well plates containing cation-adjusted Mueller Hinton broth or saline. Plates were incubated at 35° C., shaking at 150 rpm for 3 hours, after which 10 µl of Alamar Blue were added to each well and plates were incubated for 1 additional hour. After this incubation, 100 µl of a 0.03% Cetyltrimethylammonium bromide with 0.1M EDTA solution was added to each well. The plates were placed on a shaker at 450 RPM for 10 minutes, followed by centrifugation at 2500×g for 2.5 minutes. The wells were aspirated and 100 µL PBS with 0.05% Tween-20 (PBST) was added back into the wells. Ten microliters of Eu-cryptate-diamine (5 ng/well) was added to each well and the plates were shaken for 10 minutes. The plates were then centrifuged, the wells aspirated, and 200 µL 1×PBST were added to each well. These steps were repeated twice. After the final wash, time-resolved fluorescence for all wells was read at 330/615 nm.

Figure 3:
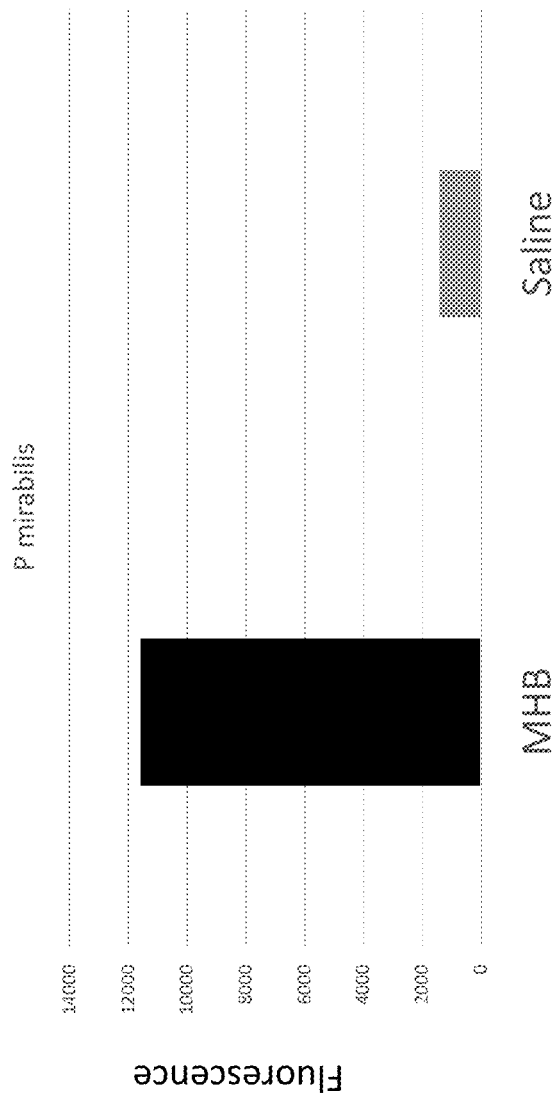
FIG. 3 shows TRF signals for *P. mirabilis* samples incubated in MHB or saline and pretreated with cetyl-trimethylammonium bromide (CTAB) prior to application of the europium-cryptate probe. As the graph indicates, CTAB treatment reveals growth in the MHB condition, indicating binding of the europium cryptate probe.

FIG. 3 shows TRF signals in the saline condition were low as expected, while signal increased in the MHB condition, indicating binding of the europium cryptate probe following CTAB pretreatment.

Example 3: Removal of the Cationic Surfactant CTAB Improves Europium-Cryptate-Diamine Binding

*S. aureus* were prepared by diluting colonies into saline to reach a McFarland value of 0.5, which was verified using a spectrophotometer, diluted, and inoculated into 96-well plates containing cation-adjusted Mueller Hinton broth and doubling dilutions of vancomycin. Plates were incubated at 35° C., shaking at 150 rpm for 3 hours, after which 10 µl of Alamar Blue were added to each well and plates were incubated for 1 additional hour. After this incubation, 100 µl of a 0.03% Cetyltrimethylammonium bromide with 0.1M EDTA solution was added to each well. The plates were placed on a shaker at 450 RPM for 10 minutes, followed by centrifugation at 2500×g for 2.5 minutes. The wells were aspirated and 100 µL PBS with 0.05% Tween-20 (PBST) or 100 µl of a 0.03% Cetyltrimethylammonium bromide with 0.1M EDTA solution was added back into the wells. Ten microliters of Eu-cryptate-diamine (5 ng/well) was added to each well and the plates were shaken for 10 minutes. The plates were then centrifuged, the wells aspirated, and 200 µL 1×PBST were added to each well. These steps were repeated twice. After the final wash, time-resolved fluorescence (TRF) for all wells was read at 330/615 nm.

Figure 4:
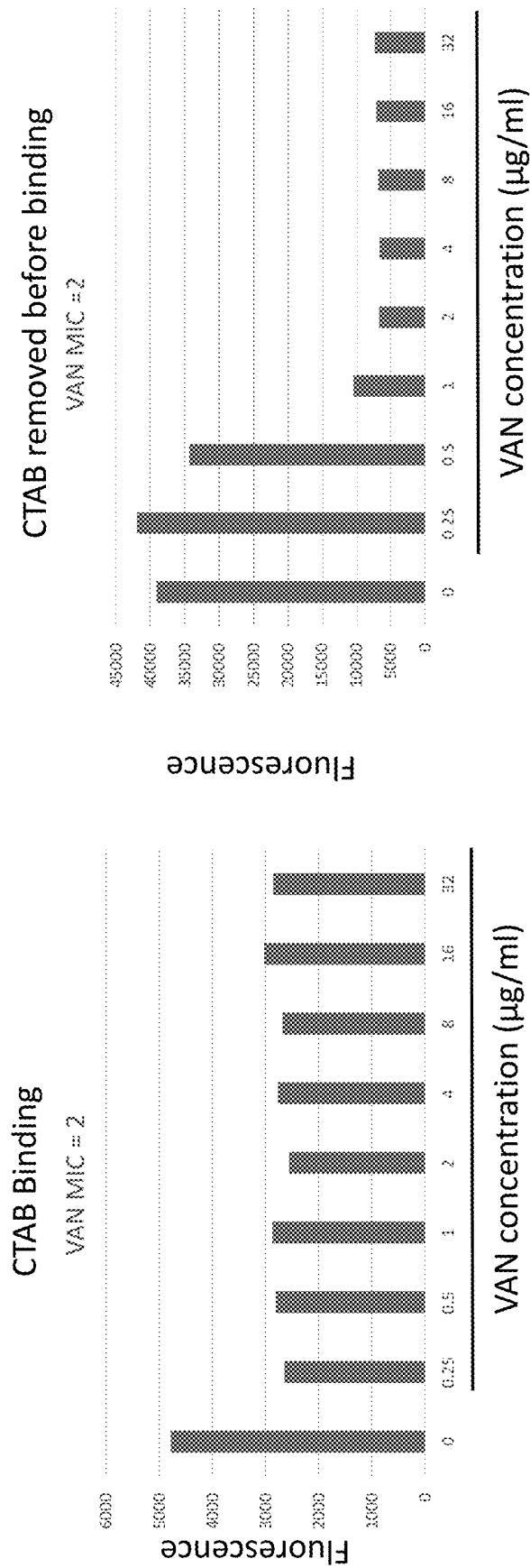
FIG. 4 shows TRF signals for CTAP treated *S. aureus* vancomycin (VAN) dilution series. In one condition, the CTAB was removed prior to application of the europium cryptate probe; in the other condition CTAB was not removed. When treated with VAN, *S. aureus* has a minimum inhibitory concentration (MIC) of 2 µg/ml. In the CTAB removal condition, shown at right, a dose dependent reduction in signal is observed and the minimum signal is observed at 2 µg/ml and lower concentrations. The same relationship is not observed in the condition where CTAB is not removed, indicating that residual CTAB may interfere with binding or signaling of the europium cryptate probe.
Figure 5:
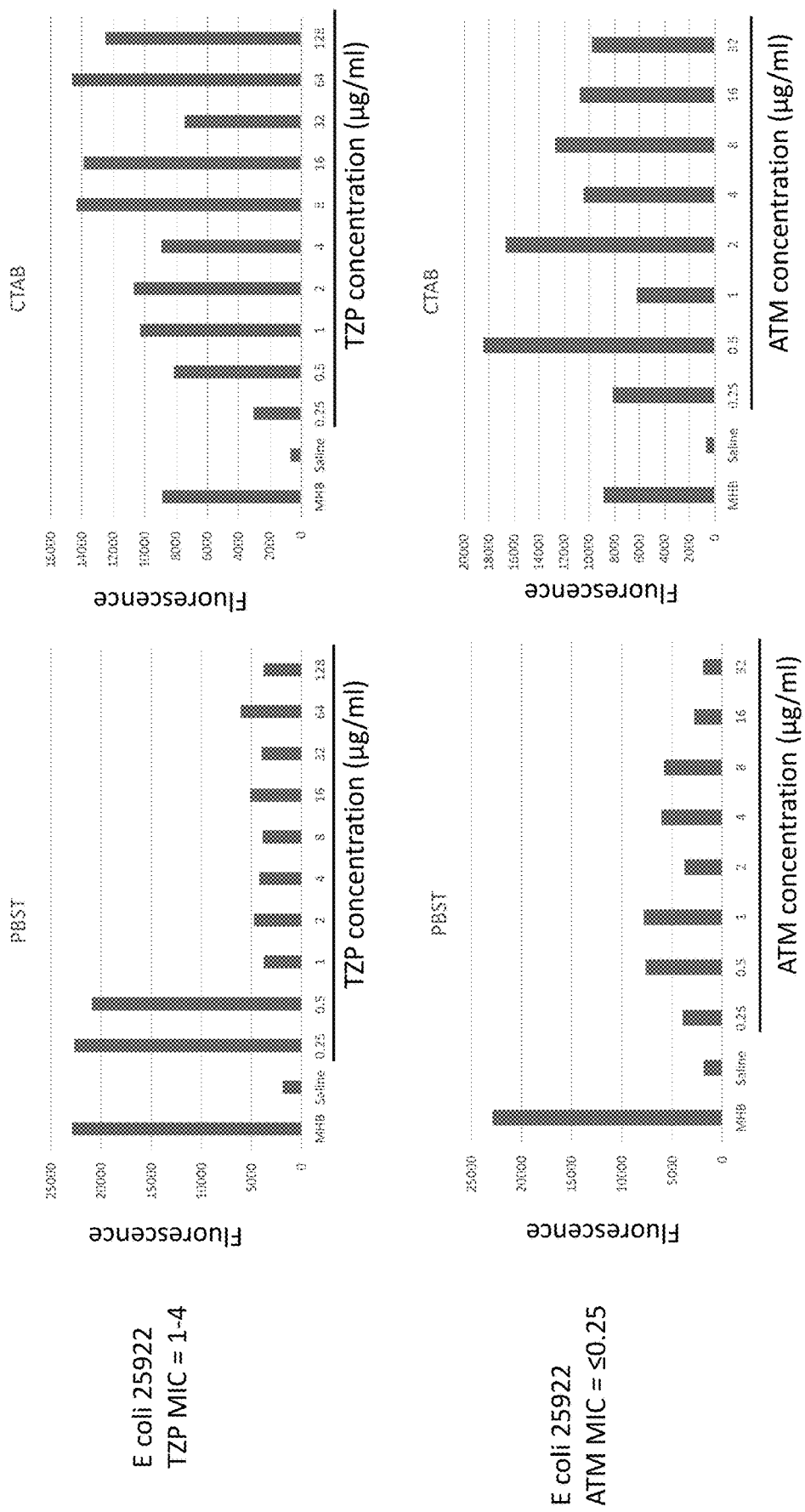
FIG. 5 shows TRF signals for *E. coli* dilution series for piperacillin-tazobactam (TZP) and azithromycin (ATM). Each dilution series includes MHB (no antimicrobial) and saline conditions, and for each antimicrobial two conditions were evaluated: pretreatment with CTAB and pretreatment with phosphate buffered saline (PBST). MIC values for TZP generally range between 1 and 4 µg/ml for the *E. coli* strain tested, while ATM MIC values are generally less than or equal to 0.25 µg/ml. A dose dependent reduction in europium cryptate probe signal is observed for the TZP dilution series pretreated with PBST; the effect is obscured when the dilution series is pretreated with CTAB. In the ATM dilution series, the lowest ATM concentration is at or above the MIC value, but similar europium cryptate probe signals are observed at all concentrations in the PBST pretreatment condition; signals in the CTAB condition were more variable with no discernable dose relationship.

As FIG. 4 shows, in the condition where CTAB was not added back, a dose-dependent response to VAN is observed, and VAN treated *S. aureus* samples appear to have a MIC of 2 µg/ml. Where CTAB was added back, however, no dose relationship was observed, indicating that CTAB may interfere with the binding or signaling of the EU-cryptate-diamine probe.

Example 4: CTAB Pretreatment of Organisms with Standard Anionic Charges Reduces Europium-Cryptate-Diamine Binding

*E. coli* were prepared by diluting colonies into saline to reach a McFarland value of 0.5, which was verified using a spectrophotometer, diluted, and inoculated into 96-well plates containing cation-adjusted Mueller Hinton broth and doubling dilutions of two antibiotics, piperacillin-tazobactam (TZP) and azitrhromycin (ATM). Plates were incubated at 35° C., shaking at 150 rpm for 3 hours, after which 10 µl of Alamar Blue were added to each well and plates were incubated for 1 additional hour. After this incubation, 100 µL of a detergent solution (either Phosphate-Buffered Saline with 1% Tween-20 or 0.03% Cetyltrimethylammonium bromide with 0.1M EDTA, was added to each well. The plates were placed on a shaker at 450 RPM for 10 minutes, followed by centrifugation at 2500×g for 2.5 minutes. The wells were aspirated and 100 µL PBS with 0.05% Tween-20 (PBST) was added back into the wells. Ten microliters of Eu-cryptate-diamine (5 ng/well) was added to each well and the plates were shaken for 10 minutes. The plates were then centrifuged, the wells aspirated, and 200 µL 1×PBST were added to each well. These steps were repeated twice. After the final wash, time-resolved fluorescence (TRF) for all wells was read at 330/615 nm.

Example 5: Anionic Ratio Predicts Appropriate Surfactant Treatment Conditions

*P. mirabilis* and *K. pneumoniae* were prepared by diluting colonies into saline to reach a McFarland value of 0.5, which was verified using a spectrophotometer, diluted, and inoculated into 96-well plates containing cation-adjusted Mueller Hinton broth and doubling dilutions of gentamycin (GEN) and ciproflaxin (CIP). Plates were incubated at 35° C., shaking at 150 rpm for 3 hours, after which 10 µl of Alamar Blue were added to each well and plates were incubated for 1 additional hour. After this incubation, Alamar Blue signal was read as the fluorescent signal Ex560/Em590. Then, 100

µL of a detergent solution (either Phosphate-Buffered Saline with 1% Tween-20 or 0.03% Cetyltrimethylammonium bromide with 0.1M EDTA, was added to each well. The plates were placed on a shaker at 450 RPM for 10 minutes, followed by centrifugation at 2500×g for 2.5 minutes. The wells were aspirated and 100 µL PBS with 0.05% Tween-20 (PBST) was added back into the wells. Ten microliters of Eu-cryptate-diamine (5 ng/well) was added to each well and the plates were shaken for 10 minutes. The plates were then centrifuged, the wells aspirated, and 200 µL 1×PBST were added to each well. These steps were repeated twice. After the final wash, time-resolved fluorescence (TRF) for all wells was read at 330/615 nm.

Figure 7:
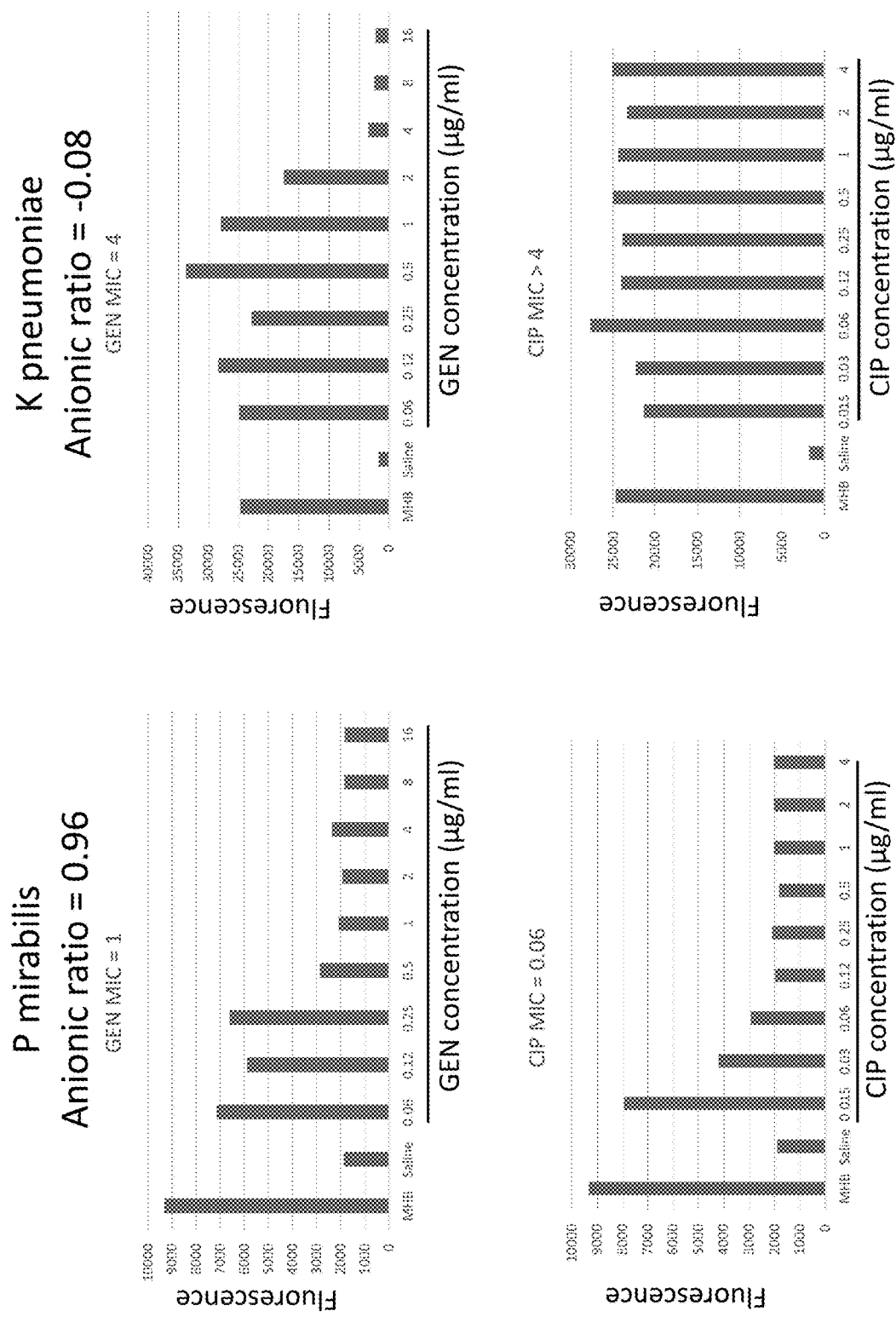
FIG. 7 shows TRF signals for gentamycin (GEN) and ciproflaxin (CIP) dilution series in *P. mirabilis* and *K. pneumoniae*. Pretreatment conditions for each microbe were selected based on anionic ratios calculated from the background subtracted fluorescent signal (Ex560/Em590) of samples grown in 4 µg/ml colistin divided by the background subtracted fluorescent signal of bacteria grown in MHB. *P. mirabilis* had an anionic ratio of 0.96, indicating low colistin sensitivity and suggesting a low surface anionic charge. The anionic ratio for *K. pneumoniae* was −0.08, suggesting a higher anionic charge. Based on these ratios, *P. mirabilis* samples were pretreated with CTAB, while *K. pneumoniae* samples were not. The dilution series showed dose relationships consistent with known MIC values for each antimicrobial, indicating that in each case the pretreatment conditions were appropriate for binding and detection of the probe.
Figure 8:
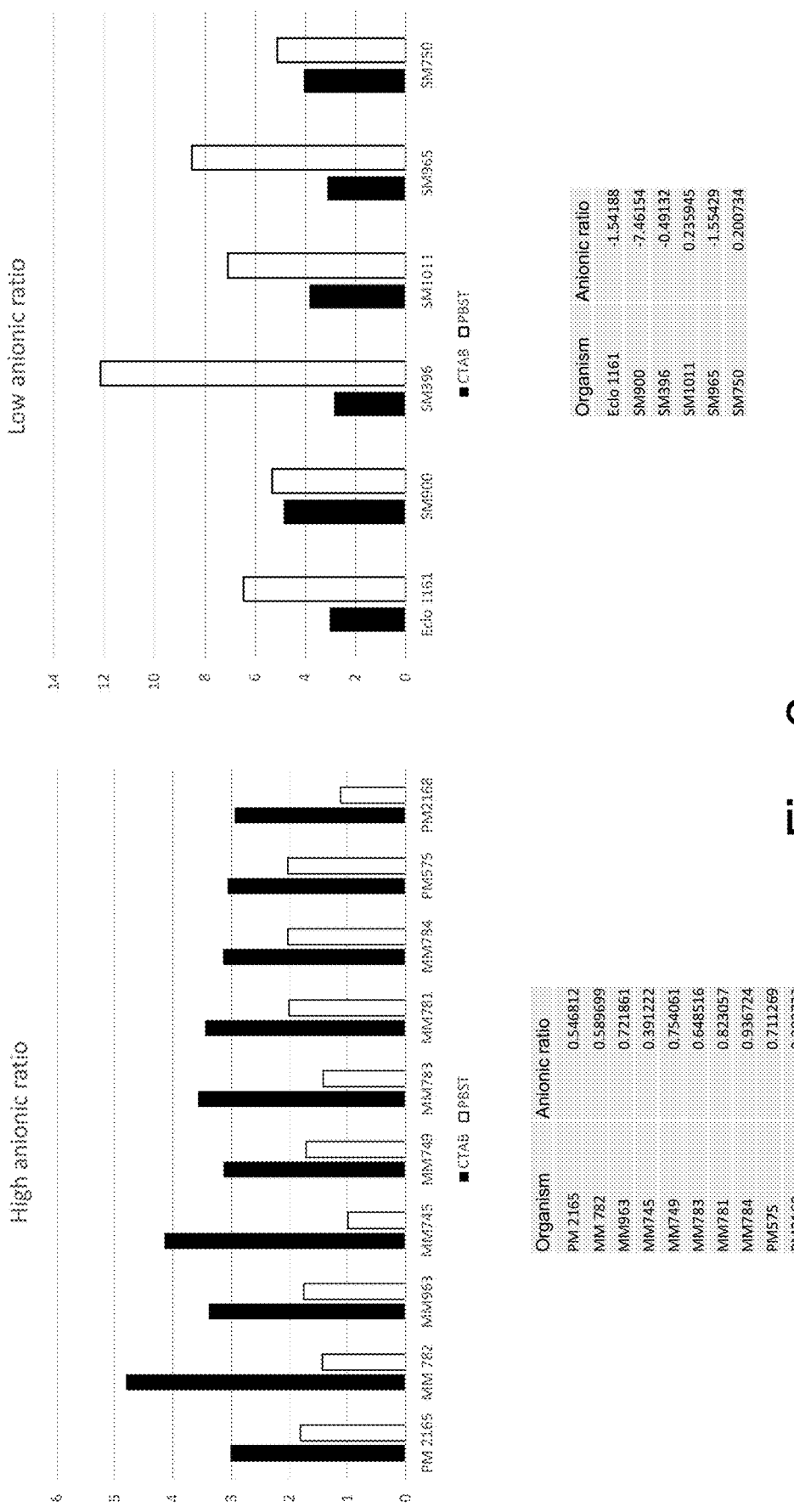
FIG. 8 depicts the ratios of the signal from wells containing the indicated organisms following surface binding with Europium-cryptate to signal from negative control uninoculated wells, after treatment with CTAB or PBST as indicated.

The anionic ratios were calculated from the background subtracted fluorescent signal (Ex560/Em590) of bacteria grown in 4 µg/ml colistin divided by the background subtracted fluorescent signal of bacteria grown in MHB. *P. mirabilis* had an anionic ration of 0.96, suggesting little or no inhibition by colistin and a reduced anionic charge, while *K. pneumoniae* had an anionic ratio of −0.08, suggesting a high degree of growth inhibition and a standard anionic charge. Accordingly, *P. mirabilis* samples were pretreated with CTAB, while *K. pneumoniae* samples received PBST. TRF signals are shown in FIG. 7, and show dose relationships consistent with known MIC values for each antimicrobial in each organism, indicating that the correct pretreatment conditions were selected based on the anionic ratio.

What is claimed is:

1. A method for performing multi-assay rapid antimicrobial susceptibility testing (AST) sequences which comprises
    (a) inoculating an AST test panel with a microbe-containing sample, wherein said AST test panel comprises
        (i) at least one positive growth control reservoir,
        (ii) at least one test reservoir that comprises a reagent that differentially affects growth of a microbe based on its anionic surface charge, and
        (iii) a plurality of reservoirs that define dilution series for a plurality of antimicrobials;
    (b) incubating said panel for a time and under conditions sufficient for microbial growth in said control reservoir to achieve or exceed a predetermined level of growth;
    (c) determining an anionic ratio for said microbe by comparing microbial growth in said test reservoir relative to microbial growth in said control reservoir;
    (d) treating the plurality of reservoirs with
        (i) a cationic surfactant if the anionic ratio is equal to or greater than a predetermined anionic ratio threshold, or
        (ii) standard assay buffer if the anionic ratio is less than the predetermined anionic ratio threshold, wherein the predetermined anionic ratio threshold is 0.05; and
    (e) treating the plurality of reservoirs with a cationic signaling agent and performing a microbe surface area assay to thereby determine the susceptibility of said microbe for said antimicrobials.

2. The method of claim 1, wherein said reagent is a cationic antimicrobial.

3. The method of claim 2, wherein said cationic antimicrobial is a polymyxin, another cationic antimicrobial peptide, a defensin or a cathelicidin.

4. The method of claim 2, wherein said cationic antimicrobial is colistin.

5. The method of claim 1, wherein said cationic surfactant is cetyl-trimethylammonium bromide (CTAB), octenidine dihydrochloride, cetylpyridinium chloride, benzalkonium chloride, dimethyldioctadecylammonium chloride, methyltrialkyl($C_8$-$C_{10}$)ammonium chloride, benzethonium chloride, cetrimonium bromide, or dioctadecyldimethylammonium bromide.

6. The method of claim 5, wherein said cationic surfactant is CTAB.

7. The method of claim 1, wherein the standard assay buffer comprises phosphate-buffered saline with 1% polysorbate 20 (PBST).

8. The method of claim 1, wherein the predetermined anionic ratio threshold is 0.1.

9. The method of claim 8, wherein the predetermined anionic ratio threshold is 0.2.

10. The method of claim 1 which comprises removing excess cationic surfactant prior to treating the plurality of reservoirs with the cationic signaling agent.

11. The method of claim 1, wherein said cationic signaling agent is a lanthanide cryptate.

12. The method of claim 1, wherein said microbe surface area assay measures an association of the cationic signaling agent with the surface of the microbe.

13. The method of claim 1, wherein at least one test reservoir comprises a cation-adjusted Mueller Hinton broth (MHB) and a fluorescent metabolic indicator; wherein at least one test reservoir comprises colistin and a fluorescent metabolic indicator; and wherein said anionic ratio is determined from the ratio of background-adjusted fluorescent signal of samples grown in colistin divided by the background-adjusted fluorescent signal of samples grown in MHB.

14. The method of claim 1, wherein said reagent is a cationic antimicrobial at a concentration at or above an epidemiological cutoff value or resistant breakpoint.

15. The method of claim 14, wherein microbial growth in said test reservoir and said positive growth control reservoir is determined by absorbance, by a metabolic indicator or by a combination thereof.

16. The method of claim 15, wherein said metabolic indicator comprises resazurin.

17. The method of claim 16, wherein resazurin is at a concentration between 10 µM and 100 mM.

18. The method of claim 16, wherein said metabolic indicator further comprises 1-methoxy-5-methlyphenazinium methyl sulfate (1-methoxy PMS) at a concentration between 50 µM and 1 M; methylene blue at a concentration between 100 nM and 5 µM; and each of ferrocyanide and ferricyanide at concentrations between 0.0001% and 0.1% (w/v).

19. The method of claim 15, wherein said cationic signaling agent is a lanthanide cryptate.

20. The method of claim 15, wherein said cationic signaling agent is a europium cryptate.

21. The method of claim 1,
    wherein said AST test panel comprises
    (a) at least two positive growth reservoirs,
    (b) at least one negative growth reservoir, and
    (c) at least one ionic character assay reservoir comprising a polycationic antimicrobial agent in an amount sufficient to result in a concentration, following inoculation, in excess of an epidemiological cutoff value or a resistant breakpoint; and
    wherein said AST test panel is loaded into an automated rapid antimicrobial susceptibility testing system for performing a multi-assay testing sequence; and
    operating the testing system to:
        add a first metabolic indicator to the negative control and positive growth reservoirs, the metabolic indicator comprising:

(i) resazurin at a concentration between 10 µM and 100 mM;
(ii) 1-methoxy-5-methlyphenazinium methyl sulfate (1-methoxy PMS) at a concentration between 50 µM and 1 M;
(iii) methylene blue at a concentration between 100 nM and 5 µM; and
(iv) each of ferrocyanide and ferricyanide at concentrations between 0.0001% and 0.1% (w/v);

incubate and optionally agitate the inoculated sample;

after a predetermined interval or after achieving or surpassing a ratio of at least 1.0 of sufficient growth, with growth being determined as the absorbance and/or fluorescence of the positive growth control-to-negative control reservoirs, add a second metabolic indicator into the ionic character assay reservoir and a positive growth control reservoir not used for determining sufficient growth;

incubate for 30 or more minutes;

determine the absorbance, fluorescence, or both, of the metabolic indicator and calculate the anionic ratio based on the ratio of microbial growth in the ionic character assay reservoir to positive growth control reservoir;

treat the plurality of reservoirs with a cationic signaling agent and perform a surface area assay to thereby determine the susceptibility of said microbe for said antimicrobials; and report at least one of a minimum inhibitory concentration of, a qualitative susceptibility interpretation for, or both for, the microbe for the plurality of antimicrobials.

22. The method of claim 21, wherein said cationic signaling agent is a lanthanide cryptate.

* * * * *